(12) United States Patent
Kuramochi et al.

(10) Patent No.: US 10,150,808 B2
(45) Date of Patent: Dec. 11, 2018

(54) MODIFIED ANTIBODY CONSTANT REGIONS

(75) Inventors: Taichi Kuramochi, Shizuoka (JP);
Shigero Tanba, Shizuoka (JP);
Tomoyuki Igawa, Shizuoka (JP);
Atsuhiko Maeda, Shizuoka (JP);
Kiyoaki Sakata, Kanagawa (JP); Mika Endoh, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/497,269

(22) PCT Filed: Sep. 24, 2010

(86) PCT No.: PCT/JP2010/066490
§ 371 (c)(1),
(2), (4) Date: Jun. 1, 2012

(87) PCT Pub. No.: WO2011/037158
PCT Pub. Date: Mar. 31, 2011

(65) Prior Publication Data
US 2012/0238729 A1    Sep. 20, 2012

(30) Foreign Application Priority Data

Sep. 24, 2009   (JP) ................................ 2009-218676

(51) Int. Cl.
| C07K 16/18 | (2006.01) |
| C07K 16/00 | (2006.01) |
| C07K 16/46 | (2006.01) |
| C07K 16/28 | (2006.01) |

(52) U.S. Cl.
CPC .......... *C07K 16/18* (2013.01); *C07K 16/2833* (2013.01); *C07K 2317/24* (2013.01); *C07K 2317/53* (2013.01); *C07K 2317/73* (2013.01); *C07K 2317/75* (2013.01)

(58) Field of Classification Search
None
See application file for complete search history.

(56) References Cited

U.S. PATENT DOCUMENTS

| 5,126,250 | A | 6/1992 | McDonough et al. |
| 5,322,678 | A | 6/1994 | Morgan et al. |
| 5,639,641 | A | 6/1997 | Pedersen et al. |
| 5,670,373 | A | 9/1997 | Kishimoto |
| 5,795,965 | A | 8/1998 | Tsuchiya et al. |
| 5,859,205 | A | 1/1999 | Adair et al. |
| 5,945,311 | A | 8/1999 | Lindhofer et al. |
| 5,990,286 | A | 11/1999 | Khawli et al. |
| 6,329,511 | B1 | 12/2001 | Vasquez et al. |
| 6,485,943 | B2 | 11/2002 | Stevens et al. |
| 6,677,436 | B1 | 1/2004 | Sato et al. |
| 6,723,319 | B1 | 4/2004 | Ito et al. |
| 6,884,879 | B1 | 4/2005 | Baca et al. |
| 6,913,747 | B1 | 7/2005 | Co et al. |
| 7,122,637 | B2 | 10/2006 | Presta |
| 7,217,797 | B2 | 5/2007 | Hinton et al. |
| 8,592,562 | B2 | 11/2013 | Kannan et al. |
| 9,096,651 | B2 | 8/2015 | Igawa et al. |
| 9,228,017 | B2 | 1/2016 | Igawa et al. |
| 2001/0001663 | A1 | 5/2001 | Kishimoto et al. |
| 2002/0142374 | A1 | 10/2002 | Gallo et al. |
| 2002/0147326 | A1* | 10/2002 | Chaikin et al. ............. 536/23.5 |
| 2002/0164339 | A1 | 11/2002 | Do et al. |
| 2002/0164668 | A1 | 11/2002 | Durham et al. |
| 2002/0187150 | A1 | 12/2002 | Mihara et al. |
| 2003/0103970 | A1 | 6/2003 | Tsuchiya |
| 2003/0190311 | A1 | 10/2003 | Dall'Acqua et al. |
| 2003/0224397 | A1 | 12/2003 | Lowman et al. |
| 2004/0071706 | A1 | 4/2004 | Ito et al. |
| 2004/0081651 | A1 | 4/2004 | Karpusas et al. |
| 2004/0236080 | A1 | 11/2004 | Aburatani et al. |
| 2005/0095243 | A1 | 5/2005 | Chan et al. |
| 2005/0130224 | A1 | 6/2005 | Saito et al. |
| 2005/0142133 | A1 | 6/2005 | Lazar et al. |
| 2005/0142635 | A1 | 6/2005 | Tsuchiya et al. |
| 2005/0191293 | A1 | 9/2005 | Deshpande et al. |
| 2005/0244403 | A1 | 11/2005 | Lazar et al. |

(Continued)

FOREIGN PATENT DOCUMENTS

| CA | 2 203 182 | 5/1996 |
| CA | 2 443 294 | 10/2002 |

(Continued)

OTHER PUBLICATIONS

Dall'Acqua et Al., Journal of Immunology, vol. 177, p. 1129-1138, 2006.*
Lazar, Molecular and Cellular Biology, vol. 8, No. 3, p. 1247-1252, 1988.*
Ju, Proceedings of the National Academy of Sciences, USA, vol. 88, p. 2658-2662, 1991.*
Bowie, Science, vol. 247, p. 1306-1310, 1990.*
Baker, Immunity, vol. 13, p. 475-484, 2000.*
Burgess, The Journal of Cell Biology, vol. 111, p. 2129-2138, 1990.*
Paul, Fundamental Immunology, 3rd Edition, 1993, pp. 292-295.*
Martinez (Biochemistry, vol. 47, p. 7496-7508, 2008).*

(Continued)

*Primary Examiner* — Michael Allen
(74) *Attorney, Agent, or Firm* — Fish & Richardson P.C.

(57) ABSTRACT

The present inventors successfully provided constant regions capable of enhancing the agonist activity of antibodies through amino acid sequence alterations. Specifically, agonist activity was found to be enhanced in antibodies having a constant region in which amino acids of the antibody heavy chain constant region are substituted or deleted, or antibodies having a constant region in which the hinge region amino acids are substituted. Use of such antibodies as pharmaceutical formulations can provide pharmaceutical formulations with improved performance.

5 Claims, 7 Drawing Sheets

Specification includes a Sequence Listing.

(56) References Cited

U.S. PATENT DOCUMENTS

| | | |
|---|---|---|
| 2005/0261229 A1 | 11/2005 | Gillies et al. |
| 2006/0019342 A1 | 1/2006 | Dall Acqua et al. |
| 2006/0024298 A1 | 2/2006 | Lazar et al. |
| 2006/0063228 A1 | 3/2006 | Kasaian et al. |
| 2006/0134709 A1 | 6/2006 | Stavenhagen et al. |
| 2006/0141456 A1 | 6/2006 | Edwards et al. |
| 2006/0160184 A1 | 7/2006 | Hoogenboom et al. |
| 2006/0194280 A1 | 8/2006 | Dillon et al. |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0036799 A1 | 2/2007 | Stavenhagen et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0110757 A1 | 5/2007 | Wei et al. |
| 2007/0134234 A1 | 6/2007 | Smith et al. |
| 2007/0148163 A1* | 6/2007 | Takahashi .......... C07K 16/2878 424/131.1 |
| 2007/0148164 A1 | 6/2007 | Farrington et al. |
| 2008/0063635 A1 | 3/2008 | Takahashi et al. |
| 2008/0166756 A1 | 7/2008 | Tsuchiya et al. |
| 2009/0208416 A1* | 8/2009 | Moretta .......... C07K 16/2851 424/9.2 |
| 2009/0221803 A1* | 9/2009 | Dall'Acqua .......... C07K 16/00 530/387.3 |
| 2009/0263392 A1 | 10/2009 | Igawa et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0239577 A1 | 9/2010 | Igawa et al. |
| 2010/0286374 A1 | 11/2010 | Kannan |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0076275 A1 | 3/2011 | Igawa et al. |
| 2011/0111406 A1 | 5/2011 | Igawa et al. |
| 2011/0129459 A1 | 6/2011 | Kuramochi et al. |
| 2011/0236374 A1 | 9/2011 | Shitara et al. |
| 2011/0245473 A1* | 10/2011 | Igawa .......... C07K 16/2866 530/389.1 |
| 2011/0287009 A1 | 11/2011 | Scheer et al. |
| 2012/0010387 A1 | 1/2012 | Niwa et al. |
| 2012/0028304 A1* | 2/2012 | Dahiyat .......... C07H 21/00 435/69.6 |
| 2012/0065379 A1 | 3/2012 | Igawa et al. |
| 2012/0071634 A1 | 3/2012 | Igawa et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |
| 2013/0052196 A1 | 2/2013 | Apostolou et al. |
| 2013/0101581 A1 | 4/2013 | Kuramochi et al. |
| 2013/0115208 A1 | 5/2013 | Ho et al. |
| 2013/0195849 A1 | 8/2013 | Spreter et al. |
| 2014/0112883 A1 | 4/2014 | Ponath et al. |
| 2014/0303356 A1 | 10/2014 | Gramer et al. |
| 2014/0377253 A1 | 12/2014 | Harding et al. |
| 2015/0274809 A1 | 10/2015 | Igawa et al. |
| 2015/0284465 A1 | 10/2015 | Igawa et al. |
| 2015/0315278 A1 | 11/2015 | Igawa et al. |
| 2016/0159915 A1 | 6/2016 | Igawa et al. |
| 2016/0229915 A1 | 8/2016 | Igawa et al. |
| 2017/0275332 A1 | 9/2017 | Igawa et al. |
| 2017/0283483 A1 | 10/2017 | Igawa et al. |
| 2017/0342154 A1 | 11/2017 | Igawa et al. |

FOREIGN PATENT DOCUMENTS

| | | |
|---|---|---|
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 700 986 | 4/2009 |
| CN | 101198698 | 6/2008 |
| CN | 102471378 | 5/2012 |
| EP | 0 637 593 | 2/1995 |
| EP | 0 783 893 | 7/1997 |
| EP | 0 811 691 | 12/1997 |
| EP | 1 069 185 | 1/2001 |
| EP | 1 510 943 | 3/2005 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 900 814 | 3/2008 |
| EP | 2 006 381 | 12/2008 |
| EP | 2 009 101 | 12/2008 |
| EP | 2 031 064 | 3/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2409991 | 1/2012 |
| EP | 2 522 724 | 11/2012 |
| EP | 2 543 727 | 1/2013 |
| EP | 2 905 290 | 8/2015 |
| EP | 2 914 634 | 9/2015 |
| JP | 2-028200 | 1/1990 |
| JP | 07-67688 | 3/1995 |
| JP | H08-500979 | 2/1996 |
| JP | 09506001 | 6/1997 |
| JP | H11-500915 | 1/1999 |
| JP | H11-500916 | 1/1999 |
| JP | 2002-514406 | 5/2002 |
| JP | 2004-86862 | 3/2004 |
| JP | 2004-511426 | 4/2004 |
| JP | 2005-535341 | 11/2005 |
| JP | 2005/537009 | 12/2005 |
| JP | 2008-512995 | 5/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-510281 | 5/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 5717624 | 5/2015 |
| JP | 2015-130883 | 7/2015 |
| JP | 5787446 | 9/2015 |
| KR | 2010/0074221 | 7/2010 |
| RU | 94028282 | 7/1996 |
| RU | 2232773 | 7/2004 |
| RU | 2266298 | 12/2005 |
| WO | WO91/01335 | * 2/1991 |
| WO | WO 92/19759 | 11/1992 |
| WO | WO 94/05690 | 3/1994 |
| WO | WO 95/014710 | 6/1995 |
| WO | WO 95/33844 | 12/1995 |
| WO | WO 96/11020 | 4/1996 |
| WO | WO 96/12503 | 5/1996 |
| WO | WO 96/27011 | 9/1996 |
| WO | WO 97/09351 | 3/1997 |
| WO | WO 97/10354 | 3/1997 |
| WO | WO 98/03546 | 1/1998 |
| WO | WO 98/50431 | 11/1998 |
| WO | WO 99/03495 | 1/1999 |
| WO | WO 1999/018212 | 4/1999 |
| WO | WO 99/51743 | 10/1999 |

(56) References Cited

FOREIGN PATENT DOCUMENTS

| | | |
|---|---|---|
| WO | WO 99/58572 | 11/1999 |
| WO | WO 01/30854 | 5/2001 |
| WO | WO 01/82899 | 11/2001 |
| WO | WO 02/072605 | 9/2002 |
| WO | WO 2003/000883 | 1/2003 |
| WO | WO 03/020949 | 3/2003 |
| WO | WO 03/105757 | 12/2003 |
| WO | WO 2004/016740 | 2/2004 |
| WO | WO 2004/020579 | 3/2004 |
| WO | WO 2004/068931 | 8/2004 |
| WO | WO 2004/096273 | 11/2004 |
| WO | WO 2004/113387 | 12/2004 |
| WO | WO 2005/005604 | 1/2005 |
| WO | WO 2005/035756 | 4/2005 |
| WO | WO 2005/047327 | 5/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/112564 | 12/2005 |
| WO | WO 2005/123126 | 12/2005 |
| WO | WO 2006/004663 | 1/2006 |
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047350 | 5/2006 |
| WO | WO 2006/050491 | 5/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/060411 | 5/2007 |
| WO | WO 2007/108559 | 9/2007 |
| WO | WO 2007/114319 | 10/2007 |
| WO | WO 2007/114325 | 10/2007 |
| WO | WO 2008/090960 | 7/2008 |
| WO | WO 2008/092117 | 7/2008 |
| WO | WO 2008/119353 | 10/2008 |
| WO | WO 2008/145141 | 12/2008 |
| WO | WO 2009/041062 | 4/2009 |
| WO | WO 2009/041613 | 4/2009 |
| WO | WO 2009/041621 | 4/2009 |
| WO | WO2009/041621 * | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/089004 | 7/2009 |
| WO | WO 2009/100309 | 8/2009 |
| WO | WO 2009/125825 | 10/2009 |
| WO | WO 2010/063746 | 6/2010 |
| WO | WO 2010/064090 | 6/2010 |
| WO | WO2010/064090 * | 6/2010 |
| WO | WO 2010/107109 | 9/2010 |
| WO | WO 2010/107110 | 9/2010 |
| WO | WO 2010/115589 | 10/2010 |
| WO | WO 2010/151792 | 12/2010 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/131746 | 10/2011 |
| WO | WO 2011/133886 | 10/2011 |
| WO | WO 2011/143545 | 11/2011 |
| WO | WO 2012/145238 | 10/2012 |
| WO | WO 2013/060867 | 5/2013 |
| WO | WO 2013/157954 | 10/2013 |
| WO | WO 2014/028354 | 2/2014 |
| WO | WO 2014/054804 | 4/2014 |
| WO | WO 2014/067011 | 5/2014 |
| WO | WO 2015/046467 | 4/2015 |
| WO | WO 2016/159213 | 10/2016 |

OTHER PUBLICATIONS

Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).

Allen et al., "Interchain disulfide bonding in human IgG2 antibodies probed by site-directed mutagenesis," *Biochemistry*, 48(17):3755-66 (2009).

Amersham Biosciences, "Protein Purification Handbook," Edition AC, 98 pages (2001).

Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).

Lansdorp et al., "Purification and analysis of bispecific tetrameric antibody complexes," *Mol. Immunol.*, 27:659-666 (1990).

Morimoto et al., "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Methods*, 24:107-117 (1992).

Presta, "Engineering of therapeutic antibodies to minimize immunogenicity and optimize function," *Adv. Drug Deliv. Rev.*, 58(5-6):640-56 (2006).

Suresh et al., "Bispecific monoclonal antibodies from hybrid hybridomas," Methods Enzymol., 121:210-228 (1986).

Warnaar et al., "Purification of bispecific F(ab')2 from murine trinoma OC/TR with specificity for CD3 and ovarian cancer," *Hybridoma*, 13:519-526 (1994).

USPTO Non-Final Office Action U.S. Appl. No. 12/680,082, dated Feb. 14, 2013, 12 pages.

USPTO Restriction Requirement in U.S. Appl. No. 13/257,145, dated Mar. 20, 2013, 11 pages.

Fish & Richardson P.C., Preliminary Amendment and Response to Restriction Requirement dated Mar. 20, 2013 in U.S. Appl. No. 13/257,145, filed Apr. 22, 2013, 7 pages.

Igawa et al., "Engineering the variable region of therapeutic IgG antibodies," *MAbs*, 3(3):243-52 (2011).

Igawa et al., "Reduced elimination of IgG antibodies by engineering the variable region," *Protein Eng. Des. Sel.*, 23(5):385-92 (2010).

Maeda et al., "pH-dependent receptor/ligand dissociation as a determining factor for intracellular sorting of ligands for epidermal growth factor receptors in rat hepatocytes," *J. Control Release*, 82(1):71-82 (2002).

Maxfield et al., "Endocytic recycling," *Nat. Rev. Mol. Cell Biol.*, 5(2):121-32 (2004).

Murtaugh et al., "A combinatorial histidine scanning library approach to engineer highly pH-dependent protein switches," *Protein Sci.*, 20(9):1619-31 doi:10.1002/pro 696 (2011).

European Search Report for App. Ser. No. EP 09 72 9337, dated Nov. 3, 2011, 3 pages.

International Search Report for App. Ser. No. PCT/JP2010/066490, dated Nov. 9, 2010, 5 pages.

Manz et al., Bioanalytical Chemistry, World Scientific Publishing Co. (2003).

Smans et al., "Bispecific antibody-mediated lysis of primary cultures of ovarian carcinoma cells using multiple target antigens," *Int. J. Cancer*, 83:270-277 (1999).

USPTO Non-Final Office Action in U.S. Appl. No. 12/295,075, dated Jun. 7, 2013, 17 pages.

(56) References Cited

OTHER PUBLICATIONS

Wang et al., "Polyethylene Glycol-modified Chimeric Toxin Composed of Transforming Growth Factor alpha and *Pseudomonas* Exotoxin," *Cancer. Res.*, 53:4588-4594 (1993).
Fish & Richardson P.C., Fourth Preliminary Amendment and Response to Restriction Requirement dated Jun. 6, 2012 in U.S. Appl. No. 12/680,082, filed Jun. 29, 2012, 13 pages.
International Preliminary Report on Patentability for App. Ser. No. PCT/JP2010/066490, dated Apr. 11, 2012, 6 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/680,082, dated Jun. 6, 2012, 12 pages.
Fish & Richardson P.C., Amendment in Reply to Action dated Jan. 3, 2013 in U.S. Appl. No. 12/679,922, filed Jul. 2, 2013, 18 pages.
USPTO Non-Final Office Action in U.S. Appl. No. 13/257,145, dated Jul. 2, 2013, 20 pages.
USPTO Restriction Requirement in U.S. Appl. No. 12/680,082, dated Sep. 14, 2012, 6 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
Burges et al., "Effective relief of malignant ascites in patients with advanced ovarian cancer by a trifunctional anti-EpCAM x anti-CD3 antibody: a phase I/II study," *Clin. Cancer Res.*, 13(13):3899-905 (2007).
Dall'Acqua et al., "Modulation of the effector functions of a human IgG1 through engineering of its hinge region," *J. Immunol.*, 177(2):1129-38 (2006).
Elliott et al., "Activation of the erythropoietin (EPO) receptor by bivalent anti-EPO receptor antibodies," *J. Biol. Chem.*, 271(40):24691-7 (1996).
Kai et al., "Switching constant domains enhances agonist activities of antibodies to a thrombopoietin receptor," *Nat. Biotechnol.*, 26(2):209-11 (2008).
Kim et al., "Mapping the site on human IgG for binding of the MHC class I-related receptor, FcRn," *Eur. J. Immunol.*, 29(9):2819-25 (1999).
Kobayashi et al., "A monoclonal antibody specific for a distinct region of hen egg-white lysozyme," *Mol. Immunol.*, 19:619-30 (1982).
Lindhofer et al., "Preferential species-restricted heavy/light chain pairing in rat/mouse quadromas. Implications for a single-step purification of bispecific antibodies," *J. Immunol.*, 155(1):219-25 (1995).
Morell et al., "Metabolic properties of IgG subclasses in man," *J. Clin. Invest.*, 49(4):673-80 (1970).
Ozhegov et al., Tolkovyi Slovar Russkogo iazyka: 2004, p. 292 (with an English translation of the corresponding part only).
Rudikoff et al., "Single amino acid substitution altering antigen-binding specificity," *Proc. Natl. Acad. Sci. U.S.A.*, 79(6):1979-83 (1982).
Ruf et al., "Pharmacokinetics and in vivo stability of intraperitoneally administered therapeutic antibody catumaxomab," *J. Clin. Oncol.*, 26 (May 20 suppl) (2008), abstr 14006.

Salfeld et al., "Isotype selection in antibody engineering," *Nat. Biotechnol.*, 25:1369-72 (2007).
USPTO Restriction Requirement in U.S. Appl. No. 12/679,922, dated Oct. 2, 2012, 9 pages.
USPTO Non-Final Office Action in U.S. Appl. No. 12/936,587, dated Nov. 7, 2012, 13 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Response to Restriction Requirement dated Oct. 2, 2012 in U.S. Appl. No. 12/679,922, filed Nov. 1, 2012, 2 pages.
International Preliminary Report on Patentability for App. Ser. No. PCT/JP2010/073361, dated Aug. 14, 2012, 7 pages.
Fish & Richardson P.C., Amendment and Response to Election Requirement dated Sep. 14, 2012 in U.S. Appl. No. 12/680,082, filed Nov. 8, 2012, 14 pages.
Bayry et al., "Immuno affinity purification of foot and mouth disease virus type specific antibodies using recombinant protein adsorbed to polystyrene wells," *J. Virol. Methods*, 81:21-30 (1999).
Fish & Richardson P.C., Supplemental Amendment in U.S. Appl. No. 11/910,128, filed Nov. 14, 2012, 20 pages.
USPTO Non-Final Office Action in U.S. Appl. No. 13/595,139, dated Nov. 14, 2012, 10 pages.
U.S. Appl. No. 13/582,073, filed Aug. 31, 2012, Kuramochi et al.
Adams et al., "Humanization of a recombinant monoclonal antibody to produce a therapeutic HER dimerization inhibitor, pertuzumab," *Cancer Immunol. Immunother.*, 55:717-727 (2006).
Amersham Biosciences, "Affinity Chromatography: Principles and Methods," Edition AD, pp. 16-18, 137 (2002).
Armour et al., "Recombinant human IgG molecules lacking Fcgamma receptor I binding and monocyte triggering activities," *Eur. J. Immunol.*, 29(8):2613-24 (1999).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al "Immunogenicity, efficacy, and adverse events of adalimumab in RA patients," *Rheumatol. Int.*, 27:269-274 (2007).
Binz et al., "Engineering novel binding proteins from nonimmunoglobulin domains," *Nat. Biotechnol.*, 23:1257-68 (2005)
Brown et al., "Tolerance of single, but not multiple, amino acid replacements in antibody $V_H$CDR 2: a means of minimizing B cell wastage from somatic hypermutation?," *J. Immunol.*, 156(9):3285-91 (1996).
Chau et al., "HuM291(Nuvion), a humanized Fc receptor-nonbinding antibody against CD3, anergizes peripheral blood T cells as partial agonist of the T cell receptor," *Transplantation.*, 71(7):941-50 (2001).
Chirino et al., "Minimizing the immunogenicity of protein therapeutics," *Drug Discov. Today.*, 9:82-90 (2004).
Chu et al., "Accumulation of succinimide in a recombinant monoclonal antibody in mildly acidic buffers under elevated temperatures," *Pharm. Res.*, 24(6):1145-56 (2007).
Cole et al., "Human IgG2 variants of chimeric anti-CD3 are nonmitogenic to T cells," *J. Immunol.*, 159(7):3613-21 (1997).
Cordoba et al., "Non-enzymatic hinge region fragmentation of antibodies in solution," *J. Chromatogr. B. Analyt. Technol. Biomed. Life Sci.*, 818(2):115-21 (2005).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Dall'Acqua et al., "Antibody humanization by framework shuffling," *Methods*, 36(1):43-60 (2005).
Deng et al., "An Agonist Murine Monoclonal Antibody to the Human c-Mpl Receptor Stimulates Megakaryocytopoiesis," *Blood*, 92:1981-88 (1998).
Dillon et al., "Structural and functional characterization of disulfide isoforms of the human IgG2 subclass," *J. Biol. Chem.*, 283(23):16206-15 (2008).
Ewert et al., "Stability improvement of antibodies for extracellular and intracellular applications: CDR grafting to stable frameworks and structure-based framework engineering," *Methods*, 34:184-199 (2004).

(56) References Cited

OTHER PUBLICATIONS

Gessner et al., "The IgG Fc receptor family," *Ann Hematol.*, 76(6):231-48 (1998).
Ghetie et al., "Increasing the serum persistence of an IgG fragment by random mutagenesis," *Nat. Biotechnol.*, 15:637-640 (1997).
Ghetie et al., "FcRn: the MHC class I-related receptor that is more than an IgG transporter," *Immunol. Today*, 18:592-598 (1997).
Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).
Graves et al., "Molecular modeling and preclinical evaluation of the humanized NR-LU-13 antibody," *Clin. Cancer Res.*, 5:899-908 (1999).
Guyre et al., "Increased potency of Fc-receptor-targeted antigens," *Cancer Immunol. Immunother.*, 45(3-4):146-8 (1997).
He et al., "Humanization and pharmacokinetics of a monoclonal antibody with specificity for both E- and P-selectin," *J. Immunol.*, 160:1029-35 (1998).
Hinton et al., "An engineered human IgG1 antibody with longer serum half-life," *J. Immunol.*, 176:346-356 (2006).
Hwang et al., "Use of human germline genes in a CDR homology-based approach to antibody humanization," *Methods*, 36:35-42 (2005).
Jefferis et al., "Recognition sites on human IgG for Fc gamma receptors: the role of glycosylation," *Immunol. Lett.*, 44(2-3):111-7 (1995).
Johnson et al., "Cation exchange-HPLC and mass spectrometry reveal C-terminal amidation of an IgG1 heavy chain," *Anal. Biochem.*, 360(1):75-83 (2007).
Jones et al., "Identification and removal of a promiscuous CD4+ T cell epitope from the C1 domain of factor VIII," *Thromb. Haemost.*, 3:991-1000 (2005).
Kashmiri et al., "Generation, characterization, and in vivo studies of humanized anticarcinoma antibody CC49," *Hybridoma*, 14:461-473 (1995).
Kim et al., "Antibody Engineering for the Development of Therapeutic Antibodies," *Mol. Cells*, 20:17-29 (2005).
Lobo et al., "Antibody pharmacokinetics and pharmacodynamics," *J. Pharm. Sci.*, 93:2645-68 (2004).
MacCallum et al., "Antibody-antigen interactions: contact analysis and binding site topography," *J. Mol. Biol.*, 262:732-45 (1996).
Maini et al., "Double-blind randomized controlled clinical trial of the interleukin-6 receptor antagonist, tocilizumab, in European patients with rheumatoid arthritis who had an incomplete response to methotrexate," *Arthritis Rheum.*, 54:2817-29 (2006).
Nishimoto et al., "Interleukin 6: from bench to bedside," *Nat. Clin. Pract. Rheumatol.*, 2:619-626 (2006).
Nishimoto et al., "Humanized anti-interleukin-6 receptor antibody treatment of multicentric Castleman disease," *Blood*, 106:2627-32 (2005).
Onda et al., "Lowering the Isoelectric Point of the Fv Portion of Recombinant Immunotoxins Leads to Decreased Nonspecific Animal Toxicity without Affecting Antitumor Activity," *Cancer Res.*, 61:5070-77 (2001).
Pavlou et al., "The therapeutic antibodies market to 2008," *Eur. J. Pharm. Biopharm.*, 59(3):389-96 (2005).
Poduslo et al., "Polyamine modification increases the permeability of proteins at the blood—nerve and blood-brain barriers," *J. Neurochem.*, 66:1599-1609 (1996).
Rajpal et al., A general method for greatly improving the affinity of antibodies by using combinatorial libraries, Proc. Natl. Acad. Sci. USA, 102:8466-71 (2005).
Reddy et al., "Elimination of Fc receptor-dependent effector functions of a modified IgG4 monoclonal antibody to human CD4," *J. Immunol.*, 164(4):1925-33 (2000).
Reichert et al., "Monoclonal antibody successes in the clinic," *Nat. Biotechnol.*, 23(9):1073-8 (2005).
Rothe et al., "Ribosome display for improved biotherapeutic molecules," *Expert Opin. Biol. Ther.*, 6:177-187 (2006).
Sarmay et al., "Mapping and comparison of the interaction sites on the Fc region of IgG responsible for triggering antibody dependent cellular cytotoxicity (ADCC) through different types of human Fc gamma receptor," *Mol. Immunol.*, 29(5):633-9 (1992).
Sato et al., "Reshaping a human antibody to inhibit the interleukin 6-dependent tumor cell growth," *Cancer Res.*, 53:851-856 (1993).
Shire et al., "Challenges in the development of high protein concentration formulations," *J. Pharm. Sci.*, 93(6):1390-402 (2004).
Strand et al., "Biologic therapies in rheumatology: lessons learned, future directions," *Nat. Rev. Drug Discov.*, 6(1):75-92 (2007).
Sun et al., "Coexpression of Gas6/Ax1 in human ovarian cancers," *Oncology*, 66(6):450-7 (2004).
Tsurushita et al., "Design of humanized antibodies: From anti-Tac to Zenapax," *Methods*, 36:69-83 (2005).
Wu et al., "Development of motavizumab, an ultra-potent antibody for the prevention of respiratory syncytial virus infection in the upper and lower respiratory tract," *J. Mol. Biol.*, 368:652-665 (2007).
Xiang et al., "Study of B72.3 combining sites by molecular modeling and site-directed mutagenesis," *Protein Eng.*, 13(5):339-44 (2000).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).
Zhu et al., "MHC class I-related neonatal Fc receptor for IgG is functionally expressed in monocytes, intestinal macrophages, and dendritic cells," *J. Immunol.*, 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
USPTO Non-Final Office Action in Appl. No. 12/679,922, dated Jan. 3, 2013, 25 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
International Search Report App. Ser. No. PCT/JP2007/057058, dated May 7, 2001, 2 pages.
Fish & Richardson P.C., Amendment in Reply to Action dated Jul. 19, 2012 in U.S. Appl. No. 12/295,075, filed Jan. 17, 2013, 113 pages.
Igawa et al., "Antibody recycling by engineered pH-dependent antigen binding improves the duration of antigen neutralization," *Nat. Biotechnol.*, 28(11):1203-7 (2010).
Queen et al., "A humanized antibody that binds to the interleukin 2 receptor," *Proc. Natl. Acad. Sci. U.S.A.*, 86(24):10029-10033 (1989).
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
USPTO Final Office Action in U.S. Appl. No. 13/257,145, dated Feb. 6, 2014, 12 pages.

(56) References Cited

OTHER PUBLICATIONS

USPTO Restriction Requirement in U.S. Appl. No. 13/257,112, dated Oct. 15, 2013, 10 pages.
Fish & Richardson P.C., Amendment and Response to Election Requirement dated Oct. 15, 2013 in U.S. Appl. No. 13/257,112, filed Nov. 15, 2013, 6 pages.
USPTO Non-Final Office Action in U.S. Appl. No. 13/257,112, dated Jan. 30, 2014, 18 pages.
Fish & Richardson P.C., Amendment in Reply to Office Action dated Jul. 2, 2013 in U.S. Appl. No. 13/257,145, filed Dec. 2, 2013, 12 pages.
Hombach et al., "A CD16/CD30 bispecific monoclonal antibody induces lysis of Hodgkin's cells by unstimulated natural killer cells in vitro and in vivo," *Int J Cancer*, 55:830-6 (1993).
Roguska et al., "Humanization of murine monoclonal antibodies through variable domain resurfacing," *Proc Natl Acad Sci U.S.A.*, 91:969-73 (1994).
Staerz et al., "Hybrid hybridoma producing a bispecific monoclonal antibody that can focus effector T-cell activity," *Proc Natl Acad Sci U.S.A.*, 83:1453-7 (1986).
Aslan et al., "Engineering a novel, stable dimeric streptavidin with lower isoelectric point," *J. Biotechnol.*, 128(2):213-25 (2007).
Atwell et al., "Stable heterodimers from remodeling the domain interface of a homodimer using a phage display library," *J. Mol. Biol.*, 270:26-35 (1997).
Baerga-Ortiz et al., "Two different proteins that compete for binding to thrombin have opposite kinetic and thermodynamic profiles," *Protein Sci.*, 13(1):166-76 (2004).
Carter, "Bispecific human IgG by design," *J. Immunol. Methods*, 248:7-15 (2001).
Dumont et al., "Monomeric Fc fusions: impact on pharmacokinetic and biological activity of protein therapeutics," *BioDrugs.*, 20(3):151-60 (2006).
Gunasekaran et al., "Enhancing antibody Fc heterodimer formation through electrostatic steering effects: applications to bispecific molecules and monovalent IgG," *J. Biol. Chem.*, 285(25):19637-46 (2010).
Jendeberg et al., "Engineering of Fc(1) and Fc(3) from human immunoglobulin G to analyse subclass specificity for Staphylococcal protein A," *J. Immunol. Methods.*, 201(1):25-34 (1997).
Marti et al., "Inverse electrostatic effect: electrostatic repulsion in the unfolded state stabilizes a leucine zipper," *Biochemistry*, 43(39):12436-47 (2004).
Marvin et al., "Redesigning an antibody fragment for faster association with its antigen," Biochemistry, 42:7077-83 (2003).
Pakula et al., "Genetic Analysis of Protein Stability and Function," Annu. Rev. Genet., 23:289-310 (1989).
Ridgway et al., "'Knobs-into-holes' engineering of antibody $C_H3$ domains for heavy chain heterodimerization," *Protein Eng.*, 9:617-621 (1996).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Shields et al., "High resolution mapping of the binding site on human IgG1 for Fc gamma RI, Fc gamma RII, Fc gamma RILL, and FcRn and design of IgG1 variants with improved binding to the Fc gamma R," *J. Biol. Chem.*, 276(9):6591-604 (2001) (Epub Nov. 28, 2000).
Van Loghem et al., "*Staphylococcal* protein A and human IgG subclasses and allotypes," *Scand. J. Immunol.*, 15(3):275-8 (1982).
Jain et al., "Engineering antibodies for clinical applications," *Trends Biotechnol.*, 25(7):307-16 (2007).
Kufer et al., "A revival of bispecific antibodies," *Trends Biotechnol.*, 22(5):238-44 (2004).
Medesan et al., "Delineation of the amino acid residues involved in transcytosis and catabolism of mouse IgG1," *J Immunol.*, Mar. 1, 1997;158(5):2211-7.
Pan et al., "Blocking neuropilin-1 function has an additive effect with anti-VEGF to inhibit tumor growth," *Cancer Cell*, Jan. 2007;11(1):53-67.
Singer et al., Genes & Genomes, 1991; 67-69.
Singer et al., Genes & Genomes, 1998;1:63-64.
USPTO Notice of Allowance in U.S. Appl. No. 13/257,145, dated Jan. 9, 2015, 7 pages.
USPTO Notice of Allowance in U.S. Appl. No. 13/257,145, dated Mar. 11, 2015, 7 pages.
USPTO Notice of Allowance in U.S. Appl. No. 13/257,112, dated Feb. 23, 2015, 8 pages.
Datta-Mannan et al., "Monoclonal antibody clearance. Impact of modulating the interaction of IgG with the neonatal Fc receptor," *J Biol Chem.*, 282(3):1709-17 (2007).
Jackman et al., "Development of a two-part strategy to identify a therapeutic human bispecific antibody that inhibits IgE receptor signaling," *J Biol Chem.*, Jul. 2, 2010;285(27): 20850-9. doi: 10.1074/jbc.M110.113910. Epub May 5, 2010.
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Spiess et al., "Bispecific antibodies with natural architecture produced by co-culture of bacteria expressing two distinct half-antibodies," *Nat Biotechnol.*, Aug. 2013; 31(8):753-8. doi: 10.1038/nbt.2621. Epub Jul. 7, 2013.
Tsubaki et al., "C-terminal modification of monoclonal antibody drugs: amidated species as a general product-related substance," *Int J Biol Macromol.*, 52:139-47. doi: 10.1016/j.ijbiomac.2012.09.016. Epub Sep. 25, 2012.
Fish & Richardson P.C., Amendment in Reply to Office Action dated Feb. 6, 2014 in U.S. Appl. No. 13/257,145, filed May 6, 2014, 10 pages.
Fish & Richardson P.C., Amendment and Reply to Non-Final Office Action dated Jan. 30, 2014 in U.S. Appl. No. 13/257,112, filed Jul. 1, 2014, 12 pages.
USPTO Final Office Action in U.S. Appl. No. 13/257,112, dated Sep. 5, 2014, 16 pages.
USPTO Notice of Allowance in U.S. Appl. No. 13/257,112, dated Apr. 2, 2015, 7 pages.
Chappel et al., "Identification of a secondary Fc gamma RI binding site within a genetically engineered human IgG antibody," *J Biol Chem.*, Nov. 25, 1993;268(33):25124-31.
Chappel et al., "Identification of the Fc gamma receptor class I binding site in human IgG through the use of recombinant IgG1/IgG2 hybrid and point-mutated antibodies," *Proc Natl Acad Sci U S A.*, Oct. 15, 1991;88(20):9036-40.
Kabat et al., Sequence of Proteins of Immunological Interest, $5^{th}$ Edition 1991, p. 690 and p. 693.
Reist et al., "Human IgG2 constant region enhances in vivo stability of anti-tenascin antibody 8106 compared with its murine parent," *Clin Cancer Res.*, Oct. 1998;4(10):2495-502.
USPTO Notice of Allowance in U.S. Appl. No. 13/257,145, dated Oct. 1, 2014, 9 pages.
Wally et al., "Identification of a novel substitution in the constant region of a gene coding for an amyloidogenic kappal light chain," *Biochim Biophys Acta.*, May 31, 1999;1454(1):49-56.
Fish & Richardson P.C., Amendment and Reply to Final Office Action dated Sep. 5, 2014 in U.S. Appl. No. 13/257,112, filed Feb. 5, 2015, 6 pages.
Allard et al., "Antigen binding properties of highly purified bispecific antibodies," *Mol Immunol.*, Oct. 1992;29(10):1219-27.
Haagen et al., "Unprimed CD4+ and CD8+ T cells can be rapidly activated by a CD3 x CD19 bispecific antibody to proliferate and become cytotoxic," *Cancer Immunol Immunother.*, Dec. 1994;39(6):391-6.
Igawa et al., "VH/VL interface engineering to promote selective expression and inhibit conformational isomerization of thrombopoietin receptor agonist single-chain diabody," *Protein Eng Des Sel.*, Aug. 2010;23(8):667-77. doi: 10.1093/protein/gzq034. Epub Jun. 24, 2010.

(56) References Cited

OTHER PUBLICATIONS

IMGT Scientific charts depicting the correspondence between Eu and Kabat numberings for the human IgG constant region, created May 17, 2001 and last updated Aug. 13, 2014.
Kenanova et al., "Tailoring the pharmacokinetics and positron emission tomography imaging properties of anti-carcinoembryonic antigen single-chain Fv-Fc antibody fragments," *Cancer Res.*, Jan. 15, 2005;65(2):622-31.
Lebégue et al., "Production and characterization of hybrid monoclonal antibodies with IgG1/IgG3 double isotype," *C R Acad Sci III.*, 1990;310(9):377-82.
Lloyd et al., "The production of a bispecific anti-CEA, anti-hapten (4-amino-phthalate) hybrid-hybridoma," *J Natl Med Assoc.*, Oct. 1991;83(10):901-4.
Manzke et al., "Single-step purification of bispecific monoclonal antibodies for immunotherapeutic use by hydrophobic interaction chromatography," *J. Immunol. Methods*, 1997;208:65-73.
Marvin et al., "Recombinant approaches to IgG-like bispecific antibodies," *Acta. Pharmacol. Sin.*, Jun. 2005;26:649-58.
Michaelsen et al., "A mutant human IgG molecule with only one C1q binding site can activate complement and induce lysis of target cells," *Eur J Immunol.*, Jan. 2006;36(1):129-38.
O'Shea et al., "Peptide 'Velcro': design of a heterodimeric coiled coil," *Curr Biol.*, Oct. 1, 1993;3(10):658-67.
Raffen et al., "Reengineering immunoglobulin domain interactions by introduction of charged residues," *Protein Eng.*, Apr. 1998;11:303-9.
USPTO Notice of Allowance in U.S. Appl. No. 13/257,112, dated Aug. 26, 2015, 7 pages.
Griffin et al., "Analysis of heavy and light chain sequences of conventional camelid antibodies from Camelus dromedarius and Camelus bactrianus species," *J Immunol Methods*, Mar. 2014;405:35-46. doi: 10.1016/j.jim.2014.01.003. Epub Jan. 18, 2014.
Hamers-Casterman et al., "Naturally occurring antibodies devoid of light chains," *Nature*, Jun. 3, 1993;363(6428):446-8.
Male et al., "Antibodies" *Immunology*, 7th Edition (2006), published by Elsevier Ltd., pp. 59-86.
Roitt et al., *Immunology, M., Mir*, 5th Edition (2000), pp. 97-113.
Wang et al., "Conserved amino acid networks involved in antibody variable domain interactions," *Proteins*, Jul. 2009;76(1):99-114. doi: 10.1002/prot.22319.
Greenwood et al., "Structural motifs involved in human IgG antibody effector functions," *Eur J Immunol.*, May 1993;23(5):1098-1104.
Dall'Acqua et al., "Increasing the affinity of a human IgG1 for the neonatal Fc receptor: biological consequences," *J. Immunol.*, Nov. 1, 2002;169(9):5171-80.
Gramer et al., "Production of stable bispecific IgG1 by controlled Fab-arm exchange: scalability from bench to large-scale manufacturing by application of standard approaches," *MAbs.*, Nov.-Dec. 2013;5(6):962-73. doi: 10.4161/mabs.26233. Epub Aug. 22, 2013.
Klein et al., "Progress in overcoming the chain association issue in bispecific heterodimeric IgG antibodies," *MAbs.*, Nov.-Dec. 2012;4(6):653-63. doi: 10.4161/mabs.21379. Epub Aug. 27, 2012.
Labrijn et al., "Efficient generation of stable bispecific IgG1 by controlled Fab-arm exchange," *Pro Natl Acad Sci U S A.*, Mar. 26, 2013;110(13):5145-50. doi: 10.1073/pnas.1220145110. Epub Mar. 11, 2013.
Labrijn et al., "Species-specific determinants in the IgG CH3 domain enable Fab-arm exchange by affecting the noncovalent CH3-CH3 interaction strength," *J Immunol.*, Sep. 15, 2011; 187(6):3238-46. doi: 10.4049/jimmuno1.1003336. Epub Aug. 12, 2011.
Merchant et al., "An efficient route to human bispecific IgG," *Nat Biotechnol.*, Jul. 1998;16(7):677-81.
Rispens et al., "Dynamics of inter-heavy chain interactions in human immunoglobulin G (IgG) subclasses studied by kinetic Fab arm exchange," *J Biol Chem.*, Feb. 28, 2014;289(9):6098-109. doi: 10.1074/jbc.M113.541813. Epub Jan. 14, 2014.
Schaefer et al., "Immunoglobulin domain crossover as a generic approach for the productiono of bispecific IgG antibodies," *Proc Natl Acad Sci U S A.*, Jul. 5, 2011;108(27):11187-92. doi: 10.1073/pnas.1019002108. Epub Jun. 20, 2011.
Schuurman et al., "Normal human immunoglobulin G4 is bispecific: it has two different antigen-combining sites," *Immunology*, Aug. 1999;97(4):693-8.
Schuurman et al., "The inter-heavy chain disulfide bonds of IgG4 are in equilibrium with intra-chain disulfide bonds," *Mol Immunol.*, Jan. 2001;38(1):1-8.
Tarditi et al., "Selective high-performance liquid chromatographic purification of bispecific monoclonal antibodies," *J. Chromatogr.*, 599(1-2):13-20 (1992).
Van Der Neut Kolfschoten et al., "Anti-inflammatory activity of human IgG4 antibodies by dynamic Fab arm exchange," *Science*, Sep. 14, 2007;317(5844):1554-7.
Batra et al., "Pharmacokinetics and biodistribution of genetically engineered antibodies," *Curr Opin Biotechnol.*, Dec. 2002;13(6):603-8.
Hinton et al., "Engineered human IgG antibodies with longer serum half-lives in primates," *J Biol.Chem.*, Feb. 20, 2004;279(8):6213-6. Epub Dec. 29, 2003.
Smolen et al., "Interleukin-6: a new therapeutic target," *Arthritis Res Ther.*, 2006;8 Suppl 2: S5. Epub Jul. 28, 2006.
McPhee et al., "Engineering human immunodeficiency virus 1 protease heterodimers as macromolecular inhibitors of viral maturation," *Proc Natl Acad Sci U S A.*, Oct. 15, 1996; 93(21):11477-81.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Coloma et al., "Position effects of variable region carbohydrate on the affinity and in vivo behavior of an anti-(1→6) dextran antibody," J Immunol., Feb. 15, 1999;162(4):2162-70.
Hird et al., "Tumour localisation with a radioactively labelled reshaped human monoclonal antibody," Br J Cancer, Nov. 1991;64(5):911-4.
Hong et al., "Enhanced cellular uptake and transport of polyclonal immunoglobulin G and fab after their cationization," J Drug Target., 2000;8(2):67-77.
Li et al., "Construction and characterization of a humanized anti-human CD3 monoclonal antibody 12F6 with effective immunoregulation functions," Immunology, Dec. 2005;116(4):487-98.
Marshall et al., "Rational design and engineering of therapeutic proteins," Drug Discov Today, Mar. 1, 2003;8(5):212-21.
Pardridge et al., "Enhanced cellular uptake and in vivo biodistribution of a monoclonal antibody following cationization," J Pharm Sci., Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Sarkar et al., "Rational cytokine design for increased lifetime and enhanced potency using pH-activated "histidine switching"," Nat Biotechnol., Sep. 2002;20(9):908-13. Epub Aug. 5, 2002.
Sharifi et al., "Improving monoclonal antibody pharmacokinetics via chemical modification," Q J Nucl Med., Dec. 1998;42(4):242-9.
Tabrizi et al., "Elimination mechanisms of therapeutic monoclonal antibodies," Drug Discov Today, Jan. 2006;11(1-2):81-8.
Verhoeyen et al., "Construction of a reshaped HMFG1 antibody and comparison of its fine specificity with that of the parent mouse antibody," *Immunology*, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).

(56) References Cited

OTHER PUBLICATIONS

Almagro et al., "Humanization of antibodies," *Front Biosci.*, Jan. 1, 2008;13:1619-33.
Arndt et al., "Factors influencing the dimer to monomer transition of an antibody single-chain Fv fragment," *Biochemistry.*, Sep. 15, 1998;37(37):12918-26.
Bian et al., "Discovery of promiscuous HLA-II-restricted T cell epitopes with TEPITOPE," *Methods.*, Dec. 2004;34(4):468-75.
Branden and Tooze, "Recognition of Foreign Molecules by the Immune System," *Introduction to Protein Structure, 2d Ed.*, Garland Publishing, 1999;pp. 299-323.
Brenner et al., "Errors in genome annotation," *Trends in Genetics*, Apr. 1999;15:132-133.
CALBIOCHEM® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Chatellier et al., "Functional mapping of conserved residues located at the VL and VH domain interface of a Fab," *J Mol Biol.*, Nov. 22, 1996;264(1):1-6.
Chen et al., "Selection and Analysis of an Optimized Anti-VEGF Antibody: Crystal Structure of an Affinity-matured Fab in Complex with Antigen," *J. Mol Biol.*, Nov. 1999;293(4):865-81.
Chen et al., "Generation and analysis of random point mutations in an antibody CDR2 sequence: many mutated antibodies lose their ability to bind antigen," *J Exp Med.*, Sep. 1, 1992; 176(3):855-66.
Chen et al., "Defective secretion of an immunoglobulin caused by mutations in the heavy chain complementarity determining region 2," *J Exp Med.*, Aug. 1, 1994;180(2):577-86.
Chamow et al., "A humanized, bispecific immunoadhesin-antibody that retargets CD3+ effectors to kill HIV-1-infected cells," *J Immunol.*, Nov. 1, 1994;153(9):4268-80.
Comper et al., "Charge selectivity in kidney ultrafiltration," *Kidney Int.*, May 1995;47(5):1242-51.
Damschroder et al., "Framework shuffling of antibodies to reduce immunogenicity and manipulate functional and biophysical properties," *Mol Immunol.*, Apr. 2007;44(11):3049-60. Epub Jan. 22, 2007.
Davies et al., "Antibody VH domains as small recognition units," *Biotechnology (N Y).*, May 1995;13(5):475-9.
De Groot et al., "De-immunization of therapeutic proteins by T-cell epitope modification," *Dev Biol (Basel).*, 2005;122:171-94.
Deen et al., "Structural determinants of glomerular permeability," *Am J Physiol Renal Physiol.*, Oct. 2001;281(4):F579-96.
Del Rio et al., "An engineered penicillin acylase with altered surface charge is more stable in alkaline pH," *Ann N Y Acad Sci.*, Oct. 12, 1996;799:61-4.
Dhiman et al., "Gene expression microarrays: a 21st century tool for directed vaccine design," *Vaccine.*, Oct. 12, 2001;20(1-2):22-30.
Diaz et al., "Effects of engineering charged amino acids in the CH3 domains on antibody heavy chain dimerization," Philippine Science Letters. 2011;4(1):48-55.
Ejima et al, "Effects of Acid Exposure on the Conformation, Stability, and Aggregation of Monoclonal Antibodies," *Proteins.* Mar. 1, 2007;66(4):954-62.
Fujii et al., "Antibody affinity maturation by random mutagenesis," *Methods Mol Biol.*, 2004;248:345-59.
Gen Bank Accession No. AAG00910.2, "recombinant IgG2 heavy chain, partial [*Homo sapiens*]," May 14, 2001, 1 page.
Gerstner et al., "Sequence plasticity in the antigen-binding site of a therapeutic anti-HER2 antibody," *J Mol Biol.*, Aug. 30, 2002;321(5):851-62.
Ghetie et al., "Multiple roles for the major histocompatibility complex class I—related receptor FcRn," *Annu Rev Immunol.*, 2000;18:739-66.
Goode et al., "The glomerular basement membrane charge-selectivity barrier: an oversimplified concept?," *Nephrol Dial Transplant.*, Sep. 1996;11(9):1714-6.
Gunawardane et al., Agonistic Human Antibodies Binding to Lecithin-Cholesterol Acyltransferase Modulate High Density Lipoprotein Metabolism, The Journal of Biological Chemistry, Feb. 2016;291(6):2799-2811; published online Dec. 7, 2015, DOI 10.1074/jbc.M115.672790.
Gupta et al., "Affinity chromatography and co-chromatography of bispecific monoclonal antibody immunoconjugates," *J Biochem Biophys Methods.*, May 31, 2002;51(3):203-16.
Ito et al., "The His-probe method: effects of histidine residues introduced into the complementarity-determining regions of antibodies on antigen-antibody interactions at different pH values," *FEBS Lett.*, Aug. 31, 1992;309:85-88.
Johnson et al., "Kabat database and its applications: 30 years after the first variability plot," *Nucleic Acids Res.*, Jan. 1, 2000;28(1):214-8.
Jung et al., "The importance of framework residues H6, H7 and H10 in antibody heavy chains: experimental evidence for a new structural subclassification of antibody V(H) domains," *J Mol Biol.*, Jun. 8, 2001;309(3):701-16.
Katayose et al., "MUC1-specific targeting immunotherapy with bispecific antibodies: inhibition of xenografted human bile duct carcinoma growth," *Cancer Res.*, Sep. 15, 1996;56(18):4205-12.
Khalifa et al., "Effects on interaction kinetics of mutations at the VH-VL interface of Fabs depend on the structural context," *J Mol Recognit.*, May-Jun. 2000;13(3):127-39.
Khawli et al., "Improved tumor localization and radioimaging with chemically modified monoclonal antibodies," *Cancer Biother Radiopharm.*, Jun. 1996;11(3):203-15.
Kim et al., "Chemical modification to reduce renal uptake of disulfide-bonded variable region fragment of anti-Tac monoclonal antibody labeled with 99mTc," *Bioconjug Chem.*, May-Jun. 1999;10(3):447-53.
Kim et al., "Lowering of pI by acylation improves the renal uptake of 99mTc-labeled anti-Tac dsFv: effect of different acylating reagents," *Nucl Med Biol.*, Nov. 2002;29(8):795-801.
Kipriyanov et al., "Bispecific tandem diabody for tumor therapy with improved antigen binding and pharmacokinetics," *J Mol Biol.*, Oct. 15, 1999;293(1):41-56.
Kipriyanov et al., "Effect of domain order on the activity of bacterially produced bispecific single-chain Fv antibodies," *J Mol Biol.*, Jun. 27, 2003;330(1):99-111.
Kobayashi et al., "The pharmacokinetic characteristics of glycolated humanized anti-Tac Fabs are determined by their isoelectric points," *Cancer Res.*, Jan. 15, 1999;59(2):422-30.
Komissarov et al., "Site-specific mutagenesis of a recombinant anti-single-stranded DNA Fab. Role of heavy chain complementarity-determining region 3 residues in antigen interaction," *J Biol Chem.*, Oct. 24, 1997;272(43):26864-70.
Kontermann, "Recombinant bispecific antibodies for cancer therapy," *Acta Pharmacol Sin.*, Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," *J Gene Med.*, Jun. 2004;6(6):642-51.
Kreutz et al., "Efficient bispecific monoclonal antibody purification using gradient thiophilic affinity chromatography," *J Chromatogr B Biomed Sci Appl.*, Sep. 4, 1998;714(2):161-70.
Kumar et al., "The second PDZ domain of INAD is a type I domain involved in binding to eye protein kinase C. Mutational analysis and naturally occurring variants," *J Biol Chem.*, Jul. 6, 2001;276(27):24971-7. Epub May 7, 2001.
Kurfis et al., "Role of Arg182 in the second extracellular loop of angiotensin II receptor AT2 in ligand binding," *Biochem Biophys Res Commun.*, Oct. 5, 1999;263(3):816-9.
Le Gall et al., "Effect of linker sequences between the antibody variable domains on the formation, stability and biological activity of a bispecific tandem diabody," *Protein Eng Des Sel.*, Apr. 2004;17(4):357-66. Epub May 4, 2004.
Leong et al., "Adapting pharmacokinetic properties of a humanized anti-interleukin-8 antibody for therapeutic applications using site-specific pegylation," *Cytokine.*, Nov. 7, 2001;16(3):106-19.
Liu et al., "Functional interactions between arginine-133 and aspartate-88 in the human reduced folate carrier: evidence for a charge-pair association," *Biochem J.*, Sep. 1, 2001;358(Pt 2):511-6.

(56) References Cited

OTHER PUBLICATIONS

Liu et al., "Heterogeneity of monoclonal antibodies," *J Pharm Sci.*, Jul. 2008;97(7):2426-47.
Lund et al., "Expression and characterization of truncated forms of humanized L243 IgG1. Architectural features can influence synthesis of its oligosaccharide chains and affect superoxide production triggered through human Fcgamma receptor I," *Eur J Biochem.*, Dec. 2000;267(24):7246-56.
Maity et al., "Equilibrium unfolding of dimeric and engineered monomeric forms of lambda Cro (F58W) repressor and the effect of added salts: evidence for the formation of folded monomer induced by sodium perchlorate," *Arch Biochem Biophys.*, Feb. 1, 2005;434(1):93-107.
Martin et al., "Crystal structure at 2.8 A of an FcRn/heterodimeric Fc complex: mechanism of pH-dependent binding," *Mol Cell.*, Apr. 2001;7(4):867-77.
Martinez et al., "Disulfide connectivity of human immunoglobulin G2 structural isoforms," *Biochemistry.*, Jul. 15, 2008;47(28):7496-508. Epub Jun. 13, 2008.
Narhi et al., "Asn to Lys mutations at three sites which are N-glycosylated in the mammalian protein decrease the aggregation of *Escherichia coli*-derived erythropoietin," *Protein Eng.*, Feb. 2001; 14(2):135-40.
Nesterova et al.,"Glypican-3 as a novel target for an antibody-drug conjugate," AACR Abstract No. 656, Los Angeles, CA (Apr. 4-18, 2007).
Newman et al, "Modification of the Fc Region of a Primatized IgG Antibody to Human CD4 Retains Its Ability to Modulate CD4 Receptors but Does Not Deplete CD4 T Cells in Chimpanzees," *Clin Immunol*. Feb. 2001;98(2):164-74.
Nieba et al., "Disrupting the hydrophobic patches at the antibody variable/constant domain interface: improved in vivo folding and physical characterization of an engineered scFv fragment," *Protein Eng.*, Apr. 1997;10(4):435-44.
Nohaile et a., "Altering dimerization specificity by changes in surface electrostatics," *Proc Natl Acad Sci U S A.*, Mar. 13, 2001;98(6):3109-14. Epub Feb. 27, 2001.
Ono et al., "The humanized anti-HM1.24 antibody effectively kills multiple myeloma cells by human effector cell-mediated cytotoxicity," *Mol Immunol.*, Apr. 1999;36(6):387-95.
Pardridge et al., "Enhanced endocytosis in cultured human breast carcinoma cells and in vivo biodistribution in rats of a humanized monoclonal antibody after cationization of the protein," *J Pharmacol Exp Ther.*, Jul. 1998;286(1):548-54.
Pavlinkova et al., "Charge-modified single chain antibody constructs of monoclonal antibody CC49: generation, characterization, pharmacokinetics, and biodistribution analysis," *Nucl Med Biol.*, Jan. 1999;26(1):27-34.
Pokkuluri et al., "A domain flip as a result of a single amino-acid substitution," *Structure.*, Aug. 15, 1998;6(8):1067-73.
Pons et a., "Energetic analysis of an antigen/antibody interface: alanine scanning mutagenesis and double mutant cycles on the HyHEL-10/lysozyme interaction" *Protein Sci.*, May 1999;8(5):958-68.
Presta, "Molecular engineering and design of therapeutic antibodies," *Curr Opin Immunol.*, Aug. 2008;20(4):460-70. doi: 10.1016/j.coi.2008.06.012.
Reichert et al., "Development trends for monoclonal antibody cancer therapeutics," *Nat Rev Drug Discov.*, May 2007;6(5):349-56.
Roopenian et al., "FcRn: the neonatal Fc receptor comes of age," *Nat Rev Immunol.*, Sep. 2007;7(9):715-25.
Sal-Man et al., "Arginine mutations within a transmembrane domain of Tar, an *Escherichia coli* aspartate receptor, can drive homodimer dissociation and heterodimer association in vivo," *Biochem J.*, Jan. 1, 2005;385(Pt 1):29-36.
Schaeffer et al., "The rat glomerular filtration barrier does not show negative charge selectivity," *Microcirculation.*, Oct. 2002;9(5):329-42.

Schmitz et al., "Phage display: a molecular tool for the generation of antibodies—a review," *Placenta.*, Mar.-Apr. 2000;21 Suppl A:S106-12.
Segal et al., "Bispecific antibodies in cancer therapy," *Curr Opin Immunol.*, Oct. 1999;11(5):558-62.
Shaul et al., "Exploring the charge space of protein-protein association: a proteomic study," *Proteins.*, Aug. 15, 2005;60(3):341-52.
Smith et al., "The challenges of genome sequence annotation or 'the devil is in the details'," *Nature Biotechnology*, Nov. 1997;15:1222-1223.
Tan et al., "Contributions of a highly conserved VH/VL hydrogen bonding interaction to scFv folding stability and refolding efficiency," *Biophys J.*, Sep. 1998;75(3):1473-82.
Tan et al., "Engineering the isoelectric point of a renal cell carcinoma targeting antibody greatly enhances scFv solubility," *Immunotechnology.*, Oct. 1998;4(2):107-14.
Ten Kate et al., "Effect of isoelectric point on biodistribution and inflammation: imaging with indium-111-labelled IgG," *Eur J Nucl Med.*, 1990;17(6-8):305-9(abstract) [Database BIOSIS Accession No. 199191074220].
Teeling et al., "The biological activity of human CD20 monoclonal antibodies is linked to unique epitopes on CD20," *J Immunol.*, Jul. 1, 2006;177(1):362-71.
Thies et al., "The alternatively folded state of the antibody C(H)3 domain," *J Mol Biol.*, Jun. 22, 2001;309(5):1077-85.
Vaisitti et al., "Cationization of monoclonal antibodies: another step towards the "magic bullet"?," *J. Biol. Regul. Homeost. Agents.*, 19(3-4):105-12 (2005).
Vajdos et al., "Comprehensive functional maps of the antigen-binding site of an anti-ErbB2 antibody obtained with shotgun scanning mutagenesis," *J Mol Biol.*, Jul. 5, 2002;320(2):415-28.
Van Walle et al., "Immunogenicity screening in protein drug development," *Expert Opin Biol Ther.*, Mar. 2007;7(3):405-18.
Vargas-Madrazo et al., "An improved model of association for VH-VL immunoglobulin domains: asymmetries between VH and VL in the packing of some interface residues," *J Mol Recognit.*, May-Jun. 2003;16(3):113-20.
Wiens et al., "Somatic mutation in VH complementarity-determining region 2 and framework region 2: differential effects on antigen binding and Ig secretion," *J Immunol.*, Aug. 1, 1997;59(3):1293-302.
Wiens et al., "Mutation of a single conserved residue in VH complementarity-determining region 2 results in a severe Ig secretion defect," *J Immunol.*, Aug. 15, 2001;167(4):2179-86.
Worn et al., "Stability engineering of antibody single-chain Fv fragments," *J Mol Biol.*, Feb. 2, 2001;305(5):989-1010.
Wu et al., "Multimerization of a chimeric anti-CD20 single-chain Fv-Fc fusion protein is mediated through variable domain exchange," *Protein Eng.*, Dec. 2001;14(12):1025-33.
Wypych et al., "Human IgG2 antibodies display disulfide-mediated structural isoforms," *J Biol Chem.*, Jun. 6, 2008;283(23):16194-205. Epub Mar. 13, 2008.
Yang et al., "CDR Walking Mutagenesis for the Affinity Maturation of a Potent Human Anti-HIV-1 Antibody into the Picomolar Range," *J Mol. Biol.*, Dec. 1995;254(3):392-403.
Yang et al. "Tailoring structure-function and pharmacokinetic properties of single-chain Fv proteins by site-specific PEGylation," *Protein Eng.*, Oct. 2003;16(10):761-70.
Zhu et al., "Remodeling domain interfaces to enhance heterodimer formation," *Protein Sci.*, Apr. 1997;6(4):781-8.
Zwick et al., "The long third complementarity-determining region of the heavy chain is important in the activity of the broadly neutralizing anti-human immunodeficiency virus type 1 antibody 2F5," *J Virol.*, Mar. 2004;78(6):3155-61.
USPTO Advisory Action in U.S. Appl. No. 13/257,145, dated May 14, 2014, 5 pages.
Kabat et al., National Institute of Health, Publ'n No. 91/3242, Sequences of Proteins of Immunological Interest, vol. 1 p. 647-60 (5th ed. 1991).
Sinha et al., "Electrostatics in protein binding and function," *Curr Protein Pept Sci.*, Dec. 2002;3(6):601-14.
U.S. Appl. No. 15/490,936, filed Apr. 19, 2017, Igawa et al.
U.S. Appl. No. 15/562,186, filed Sep. 27, 2017, Igawa et al.

(56) References Cited

OTHER PUBLICATIONS

U.S. Appl. No. 15/614,842, filed Jun. 6, 2017, Igawa et al.
U.S. Appl. No. 15/617,008, filed Jun. 8, 2017, Igawa et al.
U.S. Appl. No. 15/725,692, filed Oct. 5, 2017, Igawa et al.
U.S. Appl. No. 15/782,256, filed Oct. 12, 2017, Igawa et al.
Bendig M. M., "Humanization of Rodent Monoclonal Antibodies by CDR Grafting," Methods: A Companion to Methods in Enzymology, 1995; 8:83-93.
Hattori, Introduction of ART-Ig and application to hemophilia A treatment, Chugai Seiyaku ni Okeru Dokuji no Kakushinteki Kotai Gijutsu. Dec. 2012; 18:42-57 (with English translation).
Janeway et al., Immunobiology, 5th edition. 2001: Extract from Chapter 3, pp. 93-122.
Janeway et al., Immunobiology, 5th edition. 2001: Extract from Chapter 4, pp. 123-154.
Labrijn et al., "Controlled Fab-arm exchange for the generation of stable bispecific IgG1," Nat. Protoc., Oct. 2014; 9(10):2450-63. doi: 10.1038/nprot.2014.169. Epub Sep. 25, 2014.
Murata et al., "Anti-Digoxin Fab Variants Generated by Phage Display," Mol. Biotechnol., Jun. 2013: 54(2):269-77. doi: 10.1007/s12033-012-9564-1.
Pejchal et al., "A Conformational Switch in Human Immunodeficiency Virus gp41 Revealed by the Structures of Overlapping Epitopes Recognized by Neutralizing Antibodies," J. Virol., Sep. 2009; 83(17):8451-62. doi: 10.1128/JVI.00685-09. Epub Jun. 10, 2009.
Peters et al., "Engineering an improved IgG4 molecule with reduced disulfide bond heterogeneity and increased Fab domain thermal stability," J. Biol. Chem., Jul. 13, 2012; 287(29):24525-33. doi: 10.1074/jbc.M112.369744. Epub May 18, 2012.
Petkova et al., "Enhanced half-life of genetically engineered human IgG1 antibodies in a humanized FcRn mouse model: potential application in humorally mediated autoimmune disease," Int Immunol. Dec. 2006;18(12):1759-69. Epub Oct. 31, 2006.
Raposo et al., "Epitope-specific antibody response is controlled by immunoglobulin Vh polymorphisms," J. Exp. Med., Mar. 10, 2014: 211(3):405-11. doi: 10.1084/jem.20130968. Epub Feb. 17, 2014.
Vaccaro et al., "Divergent activities of an engineered antibody in murine and human systems have implications for therapeutic antibodies," Proc Natl Acad Sci U S A. Dec. 5, 2006; 103(49):18709-14. Epub Nov. 20, 2006.
Ward et al., "Binding activities of a repertoire of single immunoglobulin variable domains secreted from *Escherichia coli*," Nature, Oct. 12, 1989; 341:544-546.

* cited by examiner

US 10,150,808 B2

MODIFIED ANTIBODY CONSTANT REGIONS

CROSS-REFERENCE TO RELATED APPLICATIONS

This application is the National Stage of International Application Serial No. PCT/JP2010/066490, filed on Sep. 24, 2010, which claims the benefit of Japanese Application Serial No. 2009-218676, filed on Sep. 24, 2009.

TECHNICAL FIELD

The present invention relates to antibody constant regions with an altered amino acid sequence, antibodies comprising these constant regions, pharmaceutical compositions comprising these antibodies, and production methods thereof.

BACKGROUND ART

Antibodies are drawing attention as pharmaceuticals as they are highly stable in blood and have low antigenicity. Among them, agonistic antibodies that recognize cell surface expressing proteins such as receptors and can elicit specific reactions to cells are considered to be useful as pharmaceuticals. Several agonistic antibodies such as those against erythropoietin receptors and those against thrombopoietin receptors (J. Biol. Chem., (1996), 271(40), 24691-24697: Non-patent Document 1) have already been reported.

Furthermore, in recent years, with the objective of antigenicity against human, half-life in blood, and such, altered antibodies produced by subjecting antibodies to some sort of amino acid sequence alteration such as substitution have been developed as pharmaceuticals. For example, there are many reports on chimeric antibodies and humanized antibodies produced by performing humanization, chimerization, and such to reduce antigenicity against human. Such humanized antibodies and chimerized antibodies are considered to have excellent properties as pharmaceuticals. In addition, to improve half-life of antibodies in blood, and such, antibody constant regions produced by altering the amino acids of human-derived antibody constant regions have been reported as well (WO 2009/041613: Patent Document 1).

However, there are no reports of altering amino acids in antibody constant regions to enhance the agonist activity of antibodies.

PRIOR ART DOCUMENTS

Non-Patent Documents

[Non-patent Document 1] J. Biol. Chem., (1996) 271(40), 24691-24697

Patent Documents

[Patent Document 1] WO 2009/041613

SUMMARY OF THE INVENTION

Problems to be Solved by the Invention

The present invention was achieved in view of the above circumstances. An objective of the present invention was to provide antibody heavy chain constant regions that can enhance the agonist activity of an antibody and antibodies comprising these constant regions and variable regions.

Means for Solving the Problems

The present inventors dedicated their research to produce antibody constant regions with enhanced agonist activity. As a result, the present inventors discovered that the agonist activity of an antibody can be enhanced by altering the amino acid sequences of the antibody heavy chain constant regions, particularly the hinge region, and reducing the flexibility of the antibody constant regions.

The present invention relates to constant regions capable of enhancing the agonist activity of an antibody, which are antibody heavy chain constant regions with altered amino acid sequences; antibodies comprising these antibody constant regions; pharmaceutical compositions comprising such antibodies; as well as production methods thereof. More specifically, the present invention provides [1] to [43] below:

[1] an antibody constant region that comprises an amino acid sequence comprising deletion of at least one amino acid in the upper hinge region in the amino acid sequence of SEQ ID NO: 32 (IgG1 constant region);

[2] the antibody constant region of [1], which comprises deletion of at least one amino acid selected from Lys at position 218, Ser at position 219, Asp at position 221, Lys at position 222, Thr at position 223, His at position 224, and Thr at position 225 (EU numbering);

[3] the antibody constant region of [1], which comprises deletion of at least one amino acid selected from Thr at position 223, His at position 224, and Thr at position 225 (EU numbering);

[4] the antibody constant region of [1], which comprises deletions of Thr at position 223, H is at position 224, and Thr at position 225 (EU numbering);

[5] the antibody constant region of [4], which further comprises deletion of Lys at position 222 (EU numbering);

[6] the antibody constant region of [4], which further comprises deletions of Asp at position 221 and Lys at position 222 (EU numbering);

[7] the antibody constant region of [4], which further comprises deletions of Lys at position 218, Ser at position 219, Asp at position 221 and Lys at position 222 (EU numbering);

[8] the antibody constant region of any one of [1] to [7], which further comprises substitutions of at least one amino acid selected from Ser at position 192, Leu at position 193, Ile at position 199, Lys at position 214, Pro at position 217, Ser at position 219, Cys at position 220, Asp at position 221, and Lys at position 222 (EU numbering) with other amino acids;

[9] the antibody constant region of [8], which comprises substitutions of Ser at position 219 and Cys at position 220 (EU numbering) with other amino acids;

[10] the antibody constant region of [8], which comprises substitutions of Ser at position 219, Cys at position 220, Asp at position 221, and Lys at position 222 with other amino acids;

[11] the antibody constant region of [8], which comprises substitutions of Lys at position 214, Pro at position 217, Ser at position 219, Cys at position 220, Asp at position 221, and Lys at position 222 (EU numbering) with other amino acids;

[12] the antibody constant region of [8], which comprises substitutions of Lys at position 214, Ser at position 219, Cys at position 220, Asp at position 221, and Lys at position 222 (EU numbering) with other amino acids;

[13] the antibody constant region of [8], which comprises substitutions of Ile at position 199, Lys at position 214, Pro at position 217, Ser at position 219, Cys at position 220, Asp at position 221, and Lys at position 222 (EU numbering) with other amino acids;

[14] the antibody constant region of [8], which comprises substitutions of Ser at position 192, Leu at position 193, Ile at position 199, Lys at position 214, Pro at position 217, Ser at position 219, Cys at position 220, Asp at position 221, and Lys at position 222 (EU numbering) with other amino acids;

[15] the antibody constant region of [8], which comprises amino acid substitutions other than those at Lys at position 214, Pro at position 217, Ser at position 219, and Cys at position 220 (EU numbering);

[16] an antibody constant region comprising the amino acid sequence of SEQ ID NO: 20 (M97);

[17] an antibody constant region comprising the amino acid sequence of SEQ ID NO: 22 (M98);

[18] an antibody constant region comprising the amino acid sequence of SEQ ID NO: 24 (M101);

[19] an antibody constant region comprising the amino acid sequence of SEQ ID NO: 26 (M132);

[20] an antibody constant region comprising the amino acid sequence of SEQ ID NO: 45 (M146);

[21] an antibody constant region comprising the amino acid sequence of SEQ ID NO: 33 (M148);

[22] an antibody constant region comprising the amino acid sequence of SEQ ID NO: 34 (M152);

[23] an antibody constant region comprising the amino acid sequence of SEQ ID NO: 39 (M167);

[24] an antibody constant region comprising the amino acid sequence of SEQ ID NO: 40 (M168);

[25] an antibody constant region comprising the amino acid sequence of SEQ ID NO: 37 (M169);

[26] an antibody constant region comprising the amino acid sequence of SEQ ID NO: 38 (M154);

[27] an antibody comprising the antibody constant region of any one of [1] to [26];

[28] an agonistic antibody comprising an antibody constant region with deletion or substitution with other amino acids of at least one amino acid in the heavy chain upper hinge region of human IgG1, which is also an antibody with enhanced agonist activity compared to the activity before introduction of said deletion or substitution;

[29] a pharmaceutical composition comprising the antibody of [27] or [28];

[30] a method of enhancing agonist activity of an antibody, comprising the step of deleting or substituting with other amino acids at least one amino acid of the upper hinge region of the heavy chain in human IgG1;

[31] a method of enhancing agonist activity of an antibody, comprising the step of deleting at least one amino acid selected from Lys at position 218, Ser at position 219, Asp at position 221, Lys at position 222, Thr at position 223, His at position 224, and Thr at position 225 (EU numbering) in the amino acid sequence of SEQ ID NO: 32 (IgG1 constant region);

[32] the method of [31], comprising the step of deleting Thr at position 223, His at position 224, and Thr at position 225 (EU numbering);

[33] the method of [32], which further comprises the step of deleting Lys at position 222 (EU numbering);

[34] the method of [33], which further comprises the step of deleting Asp at position 221 (EU numbering);

[35] the method of [34], which further comprises the step of deleting Lys at position 218 and Ser at position 219 (EU numbering);

[36] the method of any one of [31] to [35], which further comprises the step of substituting at least one amino acid selected from Ser at position 192, Leu at position 193, Ile at position 199, Lys at position 214, Pro at position 217, Ser at position 219, Cys at position 220, Asp at position 221, and Lys at position 222 (EU numbering) with other amino acids;

[37] the method of [36], which comprises the step of substituting Ser at position 219 and Cys at position 220 with other amino acids;

[38] the method of [36], which comprises the step of substituting Ser at position 219, Cys at position 220, Asp at position 221, and Lys at position 222 with other amino acids;

[39] the method of [36], which comprises the step of substituting Lys at position 214, Pro at position 217, Ser at position 219, Cys at position 220, Asp at position 221, and Lys at position 222 (EU numbering) with other amino acids;

[40] the method of [36], which comprises the step of substituting Lys at position 214, Ser at position 219, Cys at position 220, Asp at position 221, and Lys at position 222 (EU numbering) with other amino acids;

[41] the method of [36], which comprises the step of substituting Ile at position 199, Lys at position 214, Pro at position 217, Ser at position 219, Cys at position 220, Asp at position 221, and Lys at position 222 (EU numbering) with other amino acids;

[42] the method of [36], which comprises the step of substituting Ser at position 192, Leu at position 193, Ile at position 199, Lys at position 214, Pro at position 217, Ser at position 219, Cys at position 220, Asp at position 221, and Lys at position 222 (EU numbering) with other amino acids; and

[43] the method of [36], which comprises the step of substituting Lys at position 214, Pro at position 217, Ser at position 219, and Cys at position 220 (EU numbering) with other amino acids.

Effects of the Invention

The present invention provides constant regions capable of enhancing the agonist activity of an antibody. Antibodies comprising a constant region of the present invention have enhanced agonist activity. Use of antibodies comprising a constant region of the present invention as pharmaceutical formulations can provide pharmaceutical formulations with improved performance.

MODE FOR CARRYING OUT THE INVENTION

Figure 1:
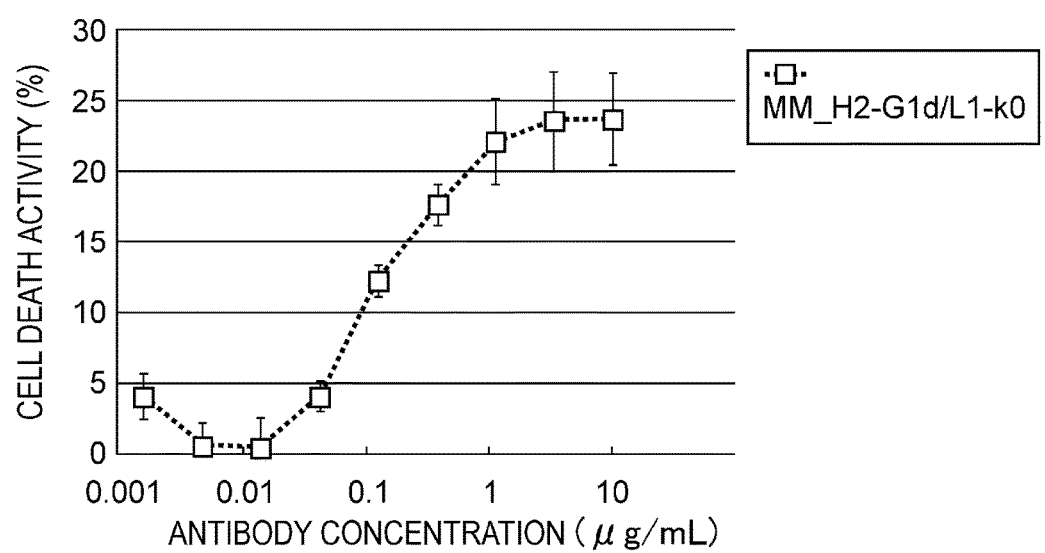
FIG. 1 presents a graph showing concentration-dependent suppression of cell growth in IM9 cells.

The present invention provides constant regions (polypeptides) capable of enhancing the agonist activity of an antibody, which are antibody heavy chain constant regions (polypeptides) with altered amino acid sequences; antibodies comprising these constant regions (polypeptides); pharmaceutical compositions comprising such antibodies; as well as production methods thereof.

There are IgG1, IgG2, IgG3, and IgG4-type constant regions for antibody heavy chain constant regions. The present invention is not particularly limited, but relates to IgG1 constant regions with altered amino acid sequences. More specifically, the present invention relates to human IgG1 constant regions with altered amino acid sequences. The amino acid sequence of the human IgG1 constant region is known (SEQ ID NO: 32).

With regard to human IgG1 constant regions of the present invention, a plurality of allotypic sequences due to genetic polymorphism are described in NIH Publication No. 91-3242 (Sequences of proteins of immunological interest), and any of them are acceptable in the present invention.

In the present invention, alteration means any one of substitution, deletion, addition, and insertion, or a combination thereof.

Furthermore, antibody heavy chain constant regions of the present invention can comprise amino acid alterations introduced based on the present invention as well as additional alterations. Additional alterations can be selected from, for example, any one of amino acid substitution, deletion, and modification, or combinations thereof. Specifically, constant regions comprising the following alterations and such in their amino acid sequence are all included in the present invention:

alterations introduced into the amino acid sequence of SEQ ID NO: 32 (human IgG1 constant region) based on the present invention;

alterations introduced into the altered amino acid sequence of SEQ ID NO: 32 (human IgG1 constant region) based on the present invention; and alterations introduced into the amino acid sequence of SEQ ID NO: 32 (human IgG1 constant region) based on the present invention, as well as additional alterations.

The hinge region of the present invention includes an upper hinge region, a middle hinge region, and a lower hinge region. The antibody heavy chain constant regions of the present invention comprise at least one amino acid deletion in the upper hinge region. Generally, the upper hinge region is the region of EU numbering 216 to 225.

Amino acid modifications of the present invention include post-translational modifications. Specific examples of post-translational modifications can include addition or deletion of sugar chains. For example, in the IgG1 constant region consisting of the amino acid sequence of SEQ ID NO: 32, the amino acid residue at position 297 (EU numbering) may be modified by sugar chains. The sugar chain structures involved in the modification are not limited. In general, antibodies expressed in eukaryotic cells include sugar chain modifications in the constant regions. Therefore, antibodies expressed in cells such as the following are usually modified by some kind of sugar chain:

antibody-producing cells of mammals; and eukaryotic cells transformed with an expression vector containing an antibody-encoding DNA.

Eukaryotic cells indicated herein include yeast and animal cells. For example, CHO cells and HEK293H cells are representative animal cells for transformation using expression vectors containing an antibody-encoding DNA. Those without sugar chain modification at this position are also included in the constant regions of the present invention. Antibodies in which the constant regions are not modified by sugar chains can be obtained by expressing the antibody-encoding gene in prokaryotic cells such as *Escherichia coli*.

<IgG1 Constant Region Having Altered Amino Acids>

The present invention provides antibody heavy chain constant regions with an altered amino acid sequence. Preferably, the present invention provides antibody constant regions capable of conferring enhanced agonist activity to the antibodies.

More specifically, the present invention provides antibody constant regions having an amino acid sequence comprising deletion of at least one amino acid of the upper hinge region in the amino acid sequence of SEQ ID NO: 32 (IgG1 constant region).

The sites where amino acids are deleted are not particularly limited, and any amino acid of the upper hinge region may be deleted.

The present invention provides antibody constant regions having an amino acid sequence comprising deletion of at least one amino acid selected from the group consisting of the following amino acids in the heavy chain constant region having the amino acid sequence of SEQ ID NO: 32 (human IgG1 constant region):

Lys at position 218 (EU numbering) (Lys at position 101 in the amino acid sequence of SEQ ID NO: 32);

Ser at position 219 (EU numbering) (Ser at position 102 in the amino acid sequence of SEQ ID NO: 32);

Asp at position 221 (EU numbering) (Asp at position 104 in the amino acid sequence of SEQ ID NO: 32);

Lys at position 222 (EU numbering) (Lys at position 105 in the amino acid sequence of SEQ ID NO: 32);

Thr at position 223 (EU numbering) (Thr at position 106 in the amino acid sequence of SEQ ID NO: 32);

His at position 224 (EU numbering) (H is at position 107 in the amino acid sequence of SEQ ID NO: 32);

Thr at position 225 (EU numbering) (Thr at position 108 in the amino acid sequence of SEQ ID NO: 32);

In the present invention, when at least one amino acid selected from the above-mentioned amino acids is deleted, the number of deleted amino acids is not particularly limited, and deletion can be carried out by selecting 1, 2, 3, 4, 5, 6, or 7 amino acids from the above-mentioned amino acids.

Deletion (i)

Preferred embodiments of the present invention include an antibody constant region having an amino acid sequence comprising deletions of Thr at position 223, His at position 224, and Thr at position 225 (EU numbering) in the heavy chain constant region (human IgG1 constant region) having the amino acid sequence of SEQ ID NO: 32. A specific example of such an antibody constant region is an antibody constant region having the amino acid sequence of SEQ ID NO: 20 (M97). While Gly (EU numbering 446) and Lys (EU numbering 447) present at the C terminus of IgG1 are missing in the amino acid sequence of SEQ ID NO: 20, these Gly and Lys can be added to the C terminus of the amino acid sequence of SEQ ID NO: 20. Therefore, another specific example of the above-mentioned antibody constant region is an antibody constant region having an amino acid sequence with additions of Gly at position 326 and Lys at position 327 in the amino acid sequence of SEQ ID NO: 20.

Deletion (ii)

Other preferred embodiments of the present invention include an antibody constant region having an amino acid sequence comprising deletions of Lys at position 222, Thr at position 223, His at position 224, and Thr at position 225 (EU numbering) in the heavy chain constant region (human IgG1 constant region) having the amino acid sequence of SEQ ID NO: 32. A specific example of such an antibody constant region is an antibody constant region having the amino acid sequence of SEQ ID NO: 39 (M167). While Gly (EU numbering 446) and Lys (EU numbering 447) present at the C terminus of IgG1 are missing in the amino acid sequence of SEQ ID NO: 39, these Gly and Lys can be added to the C terminus of the amino acid sequence of SEQ ID NO: 39. Therefore, another specific example of the above-mentioned antibody constant region is an antibody constant region having an amino acid sequence with additions of Gly at position 325 and Lys at position 326 in the amino acid sequence of SEQ ID NO: 39.

Deletion (iii)

Other preferred embodiments of the present invention include an antibody constant region having an amino acid sequence comprising deletions of Asp at position 221, Lys at position 222, Thr at position 223, His at position 224, and Thr at position 225 (EU numbering) in the heavy chain constant region (human IgG1 constant region) having the amino acid sequence of SEQ ID NO: 32. A specific example of such an antibody constant region is an antibody constant region having the amino acid sequence of SEQ ID NO: 40 (M168). While Gly (EU numbering 446) and Lys (EU numbering 447) present at the C terminus of IgG1 are missing in the amino acid sequence of SEQ ID NO: 40, these Gly and Lys can be added to the C terminus of the amino acid sequence of SEQ ID NO: 40. Therefore, another specific example of the above-mentioned antibody constant region is an antibody constant region having an amino acid sequence with additions of Gly at position 324 and Lys at position 325 in the amino acid sequence of SEQ ID NO: 40.

Deletion (iv)

Other preferred embodiments of the present invention include an antibody constant region having an amino acid sequence comprising deletions of Lys at position 218, Ser at position 219, Asp at position 221, Lys at position 222, Thr at position 223, His at position 224, and Thr at position 225 (EU numbering) in the heavy chain constant region having the amino acid sequence of SEQ ID NO: 32 (human IgG1 constant region). A specific example of such an antibody constant region is an antibody constant region having the amino acid sequence of SEQ ID NO: 37 (M169). While Gly (EU numbering 446) and Lys (EU numbering 447) present at the C terminus of IgG1 are missing in the amino acid sequence of SEQ ID NO: 37, these Gly and Lys can be added to the C terminus of the amino acid sequence of SEQ ID NO: 37. Therefore, another specific example of the above-mentioned antibody constant region is an antibody constant region having an amino acid sequence with additions of Gly at position 322 and Lys at position 323 in the amino acid sequence of SEQ ID NO: 37.

Without particular limitation, the agonist activity of antibodies can be enhanced by introducing these alterations (deletions) into the antibody heavy chain constant region.

As long as at least the above-mentioned amino acid alterations (deletions) are introduced into the heavy chain constant regions provided by the present invention, other amino acid alterations (substitutions, deletions, additions, and/or insertions) and modifications may simultaneously be introduced.

Furthermore, the present invention provides antibody heavy chain constant regions having further amino acid alterations introduced into the above-mentioned antibody heavy chain constant regions having deletions.

More specifically, the present invention provides antibody heavy chain constant regions having further substitution of at least one amino acid selected from the group consisting of:

Ser at position 192 (EU numbering) (Ser at position 75 in the amino acid sequence of SEQ ID NO: 32);
Leu at position 193 (EU numbering) (Leu at position 76 in the amino acid sequence of SEQ ID NO: 32);
Ile at position 199 (EU numbering) (Ile at position 82 in the amino acid sequence of SEQ ID NO: 32);
Lys at position 214 (EU numbering) (Lys at position 97 in the amino acid sequence of SEQ ID NO: 32);
Pro at position 217 (EU numbering) (Pro at position 100 in the amino acid sequence of SEQ ID NO: 32);
Ser at position 219 (EU numbering) (Ser at position 102 in the amino acid sequence of SEQ ID NO: 32);
Cys at position 220 (EU numbering) (Cys at position 103 in the amino acid sequence of SEQ ID NO: 32);
Asp at position 221 (EU numbering) (Asp at position 104 in the amino acid sequence of SEQ ID NO: 32); and
Lys at position 222 (EU numbering) (Lys at position 105 in the amino acid sequence of SEQ ID NO: 32)
to other amino acids in the above-mentioned antibody heavy chain constant region containing deletion of at least one amino acid selected from the group consisting of Lys at position 218, Ser at position 219, Asp at position 221, Lys at position 222, Thr at position 223, His at position 224, and Thr at position 225 (EU numbering).

In the present invention, when substituting at least one amino acid selected from the above-mentioned amino acids, the number of substituted amino acids is not particularly limited, and substitution can be carried out by selecting 1, 2, 3, 4, 5, 6, 7, 8, or 9 amino acids from the above-mentioned amino acids.

The amino acid after substitution is not particularly limited, but preferred substitutions are:
Ser at position 192 (EU numbering) with Asn;
Leu at position 193 (EU numbering) with Phe;
Ile at position 199 (EU numbering) with Thr;
Lys at position 214 (EU numbering) with Thr;
Pro at position 217 (EU numbering) with Arg;
Ser at position 219 (EU numbering) with Cys;
Cys at position 220 (EU numbering) with Ser;
Asp at position 221 (EU numbering) with Val; and
Lys at position 222 (EU numbering) with Glu.

When multiple amino acids are substituted, preferred embodiments of the combinations of amino acids to be substituted include the combinations of (1) to (7) below:

(1) substitutions of Ser at position 219 and Cys at position 220 (EU numbering) with other amino acids;
(2) substitutions of Ser at position 219, Cys at position 220, Asp at position 221, and Lys at position 222 (EU numbering) with other amino acids;
(3) substitutions of Lys at position 214, Pro at position 217, Ser at position 219, Cys at position 220, Asp at position 221, and Lys at position 222 (EU numbering) with other amino acids;
(4) substitutions of Lys at position 214, Ser at position 219, Cys at position 220, Asp at position 221, and Lys at position 222 (EU numbering) with other amino acids;
(5) substitutions of Ile at position 199, Lys at position 214, Pro at position 217, Ser at position 219, Cys at position 220, Asp at position 221, and Lys at position 222 (EU numbering) with other amino acids;
(6) substitutions of Ser at position 192, Leu at position 193, Ile at position 199, Lys at position 214, Pro at position 217, Ser at position 219, Cys at position 220, Asp at position 221, and Lys at position 222 (EU numbering) with other amino acids; and (7) substitutions of Lys at position 214, Pro at position 217, Ser at position 219, and Cys at position 220 (EU numbering) with other amino acids.

The above-mentioned amino acid deletions (i) to (iv) and the above-mentioned amino acid substitutions (1) to (7) can be combined appropriately, and any combination is acceptable in the present invention.

Examples of preferred combinations of amino acid deletions and amino acid substitutions include:

deletions of Thr at position 223, His at position 224, and Thr at position 225 (EU numbering), and substitution of Ser at position 219 and Cys at position 220 (EU numbering) with other amino acids (combination of deletion (i) and substitution (1));

deletions of Thr at position 223, His at position 224, and Thr at position 225 (EU numbering), and substitution of Ser at position 219, Cys at position 220, Asp at position 221, and Lys at position 222 (EU numbering) with other amino acids (combination of deletion (i) and substitution (2));

deletions of Thr at position 223, His at position 224, and Thr at position 225 (EU numbering), and substitution of Lys at position 214, Pro at position 217, Ser at position 219, Cys at position 220, Asp at position 221, and Lys at position 222 (EU numbering) with other amino acids (combination of deletion (i) and substitution (3));

deletions of Thr at position 223, His at position 224, and Thr at position 225 (EU numbering), and substitution of Lys at position 214, Ser at position 219, Cys at position 220, Asp at position 221, and Lys at position 222 (EU numbering) with other amino acids (combination of deletion (i) and substitution (4));

deletions of Thr at position 223, His at position 224, and Thr at position 225 (EU numbering), and substitutions of Ile at position 199, Lys at position 214, Pro at position 217, Ser at position 219, Cys at position 220, Asp at position 221, and Lys at position 222 (EU numbering) with other amino acids (combination of deletion (i) and substitution (5));

deletions of Thr at position 223, His at position 224, and Thr at position 225 (EU numbering), and substitutions of Ser at position 192, Leu at position 193, Ile at position 199, Lys at position 214, Pro at position 217, Ser at position 219, Cys at position 220, Asp at position 221, and Lys at position 222 (EU numbering) with other amino acids (combination of deletion (i) and substitution (6)); and deletions of Asp at position 221, Lys at position 222, Thr at position 223, His at position 224, and Thr at positions 225 (EU numbering), and substitution of Lys at position 214, Pro at position 217, Ser at position 219, and Cys at position 220 (EU numbering) with other amino acids (combination of deletion (iii) and substitution (7)).

Preferred embodiments of such antibody constant regions include the following antibody constant regions:

an antibody constant region having the amino acid sequence of SEQ ID NO: 22 (M98);

an antibody constant region having the amino acid sequence of SEQ ID NO: 24 (M101);

an antibody constant region having the amino acid sequence of SEQ ID NO: 26 (M132);

an antibody constant region having the amino acid sequence of SEQ ID NO: 45 (M146);

an antibody constant region having the amino acid sequence of SEQ ID NO: 33 (M148);

an antibody constant region having the amino acid sequence of SEQ ID NO: 34 (M152); and an antibody constant region having the amino acid sequence of SEQ ID NO: 38 (M154).

Furthermore, while Gly (EU numbering 446) and Lys (EU numbering 447) present at the C terminus of IgG1 are missing in the amino acid sequence of SEQ ID NO: 22, SEQ ID NO: 24, SEQ ID NO: 26, SEQ ID NO: 45, SEQ ID NO: 33, SEQ ID NO: 34, or SEQ ID NO: 38, these Gly and Lys may be added to the C terminus of the amino acid sequence of SEQ ID NO: 22, SEQ ID NO: 24, SEQ ID NO: 26, SEQ ID NO: 45, SEQ ID NO: 33, SEQ ID NO: 34, or SEQ ID NO: 38. Therefore, other specific examples of the above-mentioned antibody constant region include antibody constant regions having an amino acid sequence with additions of Gly at position 326 and Lys at position 327 (EU numbering) in the amino acid sequence of SEQ ID NO: 22, SEQ ID NO: 24, SEQ ID NO: 26, SEQ ID NO: 45 (M146), SEQ ID NO: 33 (M148), or SEQ ID NO: 34 (M152), or antibody constant regions having an amino acid sequence with additions of Gly at position 324 and Lys at position 325 (EU numbering) in the amino acid sequence of SEQ ID NO: 38 (M154).

Without particular limitation, the agonist activity of antibodies can be enhanced by introducing such substitutions into antibody heavy chain constant regions.

As long as at least the above-mentioned amino acid substitutions are introduced into the antibody heavy chain constant regions provided by the present invention, other amino acid alterations (substitutions, deletions, additions, and/or insertions, etc.) or modifications may be simultaneously introduced.

Furthermore, the present invention provides genes encoding the antibody constant regions of the present invention, vectors comprising these genes, cells comprising the vectors (host cells and such), and methods for producing an antibody constant region of the present invention by culturing these cells. The genes, vectors, cells, and production methods are as described later.

<Antibody>

Furthermore, the present invention provides antibodies comprising any of the above-mentioned heavy chain constant regions with altered amino acid sequences.

In addition, the present invention provides agonistic antibodies that comprise an antibody constant region in which at least one amino acid of the heavy chain upper hinge region in human IgG1 is deleted or substituted with other amino acids, and which have enhanced agonist activity compared to before the deletion or substitution.

A variable region constituting an antibody of the present invention can be a variable region that recognizes an arbitrary antigen. A preferred variable region in the present invention may be, for example, a variable region of an antibody having agonist activity. For example, a variable region of an anti-HLA-A antibody having agonist activity can be used as the variable region constituting an antibody of the present invention. One or more amino acid residue alterations are allowed in the amino acid sequence constituting the heavy chain variable region, as long as its antigen binding activity is maintained.

When altering the amino acid sequence of a variable region, the altered sites and number of altered amino acids are not particularly limited. For example, amino acids present in CDR and/or FR can be altered appropriately. Without particular limitation, when altering the amino acids of a variable region, it is preferred that the binding activity is maintained, and for example, it is preferable that the binding activity is 50% or more, preferably 80% or more, or more preferably 100% or more of the activity before alteration. Furthermore, binding activity may be increased by altering amino acids, and for example, the binding activity may be twice, five times, ten times, or such that before alteration. In the antibodies of the present invention, amino acid sequence alterations may be at least one of amino acid residue substitution, addition, deletion, and modification.

For example, modification of the N-terminal glutamine of the variable region to pyroglutamic acid by pyroglutamylation is a modification well-known to those skilled in the art. Therefore, when the heavy chain N terminus of the antibodies of the present invention is glutamine, the antibodies of the present invention include variable regions in which the glutamine is modified to pyroglutamic acid.

A light chain constituting an antibody of the present invention can also include any variable region. A preferred light chain variable region is a light chain variable region of an antibody from which the variable region of the heavy chain is derived. Therefore, when using a variable region contained in the amino acid sequence of H2 (SEQ ID NO: 4) for the heavy chain variable region, it is possible to combine with, for example, a light chain having the amino acid sequence of L1 (SEQ ID NO: 5).

While there are κ chain- and λ chain-type constant regions in light chain constant regions of antibodies, either of the light chain constant regions are acceptable. Furthermore, in the present invention, a light chain constant region may be a light chain constant region subjected to alterations such as amino acid substitutions, deletions, additions, and/or insertions.

An antibody of the present invention may be any antibody as long as it has the above-described antibody constant region, and the type of antigen and the origin of the antibody and such are not limited. The origin of antibodies is not particularly limited. The antibodies include human, mouse, rat, and rabbit antibodies. The antibodies of the present invention may be chimeric, humanized antibodies, or such. In a preferred embodiment, the antibodies of the present invention are humanized antibodies or human antibodies.

Furthermore, the antibody constant regions of the present invention and/or antibody molecules comprising an antibody constant region of the present invention can be linked in a form of Fc fusion molecule to antibody-like binding molecules (scaffold molecules), bioactive peptides, binding peptides, or such.

The antibody molecules of the present invention also include modification products of an antibody as long as they comprise the antibody constant regions of the present invention.

Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single antibody molecule variable regions that recognize different epitopes. The epitopes may be present in a single molecule or in separate molecules.

The antibody constant regions of the present invention can be used as a constant region in an antibody against an arbitrary antigen. The antigen is not particularly limited.

The antibodies of the present invention can be obtained by, for example, the following methods. First, an antibody that binds to the antigen of interest is obtained by methods well-known to those skilled in the art. If the obtained antibody is a non-human antibody, it can be chimerized or humanized. Then, one or more amino acid residues are deleted or altered to amino acids of interest in the constant region. Methods for altering one or more amino acid residues to amino acids of interest include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152, 271-275; Zoller, M. J., and Smith, M. Oligonucleotide-directed mutagenesis of DNA fragments cloned into M13 vectors. Methods Enzymol. (1983) 100, 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12, 9441-9456; Kramer W., and Fritz H. J. Oligonucleotide-directed construction of mutations via gapped duplex DNA Methods. Enzymol. (1987) 154, 350-367; Kunkel, T. A. Rapid and efficient site-specific mutagenesis without phenotypic selection. Proc. Natl. Acad. Sci. USA (1985) 82, 488-492). These methods can be used to alter other amino acids for target amino acids in the constant region of an antibody.

Furthermore, the present invention relates to methods for producing antibodies with altered amino acids in the heavy chain constant region, which comprises the following steps of:

(a) expressing a DNA encoding a heavy chain in which one or more amino acid residues in the constant region have been substituted with other amino acids of interest or deleted, and a DNA encoding a light chain; and (b) collecting the expression product of step (a).

More specifically, the present invention provides methods for producing antibodies comprising a heavy chain constant region of the present invention having amino acid alterations, wherein the methods comprises the following steps of:

(a) culturing host cells comprising a vector introduced with a polynucleotide encoding an antibody heavy chain containing a heavy chain constant region of the present invention having amino acid alterations; and (b) obtaining antibody heavy chain and/or antibody light chain encoded by the above-mentioned gene.

The first step in the production methods of the present invention is expressing a DNA encoding an antibody heavy chain in which one or more amino acid residues in the constant region are deleted or replaced with amino acids of interest, and a DNA encoding an antibody light chain. A DNA encoding a heavy chain in which one or more amino acid residues in the constant region are deleted or replaced with amino acids of interest can be prepared, for example, by obtaining a DNA encoding the constant region of a wild type heavy chain, and introducing an appropriate substitution so that a codon encoding a particular amino acid in the constant region encodes an amino acid of interest.

Alternatively, a DNA encoding a heavy chain in which one or more amino acid residues in the constant region are deleted or replaced with amino acids of interest can also be prepared by designing and then chemically synthesizing a DNA encoding a protein in which one or more amino acid residues in the constant region of the wild type heavy chain are deleted or replaced with amino acids of interest.

The position of amino acid substitution or deletion and the type of amino acid substitution include the substitutions or deletions described herein, but are not limited thereto.

Alternatively, a DNA encoding a heavy chain in which one or more amino acid residues in the constant region are deleted or replaced with amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. A DNA encoding a light chain can also be prepared as a combination of partial DNAs.

Methods for expressing the above-described DNAs include the methods described below. For example, a heavy-chain expression vector is constructed by inserting a DNA encoding a heavy-chain variable region into an expression vector along with a DNA encoding a heavy-chain constant region. Likewise, a light-chain expression vector is constructed by inserting a DNA encoding a light-chain variable region into an expression vector along with a DNA encoding a light-chain constant region. Alternatively, these heavy and light chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as CHO (Chinese hamster ovary) cells as well as microorganisms such as E. coli, yeast, and Bacillus subtilis, and plants and animals (Nature Biotechnology (2007) 25, 563-565; Nature Biotechnology (1998) 16, 773-777; Biochemical and Biophysical Research Communications (1999) 255, 444-450; Nature Biotechnology (2005) 23, 1159-1169; Journal of Virology (2001) 75, 2803-2809; Biochemical and Biophysical Research Communications (2003) 308, 94-100). The transformation can be preferably achieved by using electroporation, the lipofectin method (R. W. Malone et al., Proc. Natl. Acad. Sci. USA (1989) 86, 6077; P. L. Felgner et al., Proc. Natl. Acad. Sci. USA (1987) 84, 7413), calcium phosphate method (F. L. Graham & A. J. van der Eb, Virology (1973) 52, 456-467), DEAE-Dextran method, and the like.

In the next step in antibody production, the expression products obtained in step (a) are collected. The expression products can be collected, for example, by culturing the transformants and then separating the products from the transformed cells or culture media. Separation and purification of antibodies can be achieved by an appropriate combination of methods such as centrifugation, ammonium sulfate fractionation, salting out, ultrafiltration, columns of 1q, FcRn, Protein A, and Protein G, affinity chromatography, ion exchange chromatography, and gel filtration chromatography.

The present invention provides antibodies produced as described above. More specifically, the present invention relates to antibodies with enhanced agonist activity, which can be produced by the following steps:
(a) expressing in a host cell DNAs encoding an antibody heavy chain comprising an antibody variable region and an antibody constant region having amino acid alterations of the present invention, and an antibody light chain; and
(b) collecting the antibodies expressed in (a).

In the above-mentioned method, the amino acid sequence of the heavy chain constant region is a constant region provided by the present invention. In preferred embodiments of the present invention, a constant region has, for example, the following amino acid sequence:

SEQ ID NO: 20 (M97)
SEQ ID NO: 22 (M98)
SEQ ID NO: 24 (M101)
SEQ ID NO: 26 (M132)
SEQ ID NO: 45 (M146)
SEQ ID NO: 33 (M148)
SEQ ID NO: 34 (M152)
SEQ ID NO: 39 (M167)
SEQ ID NO: 40 (M168)
SEQ ID NO: 37 (M169)
SEQ ID NO: 38 (M154)

Furthermore, examples of other preferred embodiments of a constant region of the present invention include constant regions comprising the following amino acid sequences:

an amino acid sequence in which Gly is added at position 326 and Lys is added at position 327 in the sequence of SEQ ID NO: 20 (M97)

an amino acid sequence in which Gly is added at position 326 and Lys is added at position 327 in the sequence of SEQ ID NO: 22 (M98)

an amino acid sequence in which Gly is added at position 326 and Lys is added at position 327 in the sequence of SEQ ID NO: 24 (M101)

an amino acid sequence in which Gly is added at position 326 and Lys is added at position 327 in the sequence of SEQ ID NO: 26 (M132)

an amino acid sequence in which Gly is added at position 326 and Lys is added at position 327 in the sequence of SEQ ID NO: 45 (M146)

an amino acid sequence in which Gly is added at position 326 and Lys is added at position 327 in the sequence of SEQ ID NO: 33 (M148)

an amino acid sequence in which Gly is added at position 326 and Lys is added at position 327 in the sequence SEQ ID NO: 34 (M152)

an amino acid sequence in which Gly is added at position 325 and Lys is added at position 326 in the sequence SEQ ID NO: 39 (M167)

an amino acid sequence in which Gly is added at position 324 and Lys is added at position 325 in the sequence SEQ ID NO: 40 (M168)

an amino acid sequence in which Gly is added at position 322 and Lys is added at position 323 in the sequence SEQ ID NO: 37 (M169)

an amino acid sequence in which Gly is added at position 324 and Lys is added at position 325 in the sequence SEQ ID NO: 38 (M154)

A DNA encoding an antibody heavy chain can be prepared by linking a DNA encoding such an amino acid sequence with a DNA encoding a heavy chain variable region. For example, the amino acid sequences indicated in SEQ ID NOs: 21, 23, 25, 27, 29, and 31 are full-length sequences of heavy chains of humanized HLA-A-recognizing antibodies.

The constant region (129-453) in the amino acid sequence of SEQ ID NO: 21 is composed of the amino acid sequence of SEQ ID NO: 20. Meanwhile, 1-128 in SEQ ID NO: 21 correspond to the variable region.

The constant region (129-453) in the amino acid sequence of SEQ ID NO: 23 is composed of the amino acid sequence of SEQ ID NO: 22. Meanwhile, 1-128 in SEQ ID NO: 23 correspond to the variable region.

The constant region (129-453) in the amino acid sequence of SEQ ID NO: 25 is composed of the amino acid sequence of SEQ ID NO: 24. Meanwhile, 1-128 in SEQ ID NO: 25 correspond to the variable region.

The constant region (129-453) in the amino acid sequence of SEQ ID NO: 27 is composed of the amino acid sequence of SEQ ID NO: 26. Meanwhile, 1-128 in SEQ ID NO: 27 correspond to the variable region.

The constant region (129-452) in the amino acid sequence of SEQ ID NO: 46 is composed of the amino acid sequence of SEQ ID NO: 45. Meanwhile, 1-128 in SEQ ID NO: 46 correspond to the variable region.

The constant region (129-452) in the amino acid sequence of SEQ ID NO: 35 is composed of the amino acid sequence of SEQ ID NO: 33. Meanwhile, 1-128 in SEQ ID NO: 35 correspond to the variable region.

The constant region (129-452) in the amino acid sequence of SEQ ID NO: 36 is composed of the amino acid sequence of SEQ ID NO: 34. Meanwhile, 1-128 in SEQ ID NO: 36 correspond to the variable region.

The constant region (129-452) in the amino acid sequence of SEQ ID NO: 43 is composed of the amino acid sequence of SEQ ID NO: 39. Meanwhile, 1-128 in SEQ ID NO: 43 correspond to the variable region.

The constant region (129-451) in the amino acid sequence of SEQ ID NO: 44 is composed of the amino acid sequence of SEQ ID NO: 40. Meanwhile, 1-128 in SEQ ID NO: 44 correspond to the variable region.

The constant region (129-449) in the amino acid sequence of SEQ ID NO: 41 is composed of the amino acid sequence of SEQ ID NO: 37. Meanwhile, 1-128 in SEQ ID NO: 41 correspond to the variable region.

The constant region (129-451) in the amino acid sequence of SEQ ID NO: 42 is composed of the amino acid sequence of SEQ ID NO: 38. Meanwhile, 1-128 in SEQ ID NO: 42 correspond to the variable region.

A light chain comprising, for example, a λ chain constant region a κ chain constant region, or constant regions with one or more amino acid substitutions, deletions, additions, and/or insertions in these constant regions can be combined as a light chain constituting an antibody of the present invention. The DNAs encoding the heavy and light chains used for obtaining the antibodies of the present invention can be obtained, for example, by synthesizing DNAs encoding these amino acid sequences. DNAs encoding the heavy and light chains can be further attached with an additional sequence such as a signal sequence when necessary and incorporated into suitable expression vectors. The vectors may include promoters and enhancers for expressing DNAs encoding antibodies incorporated into appropriate hosts.

Furthermore, the present invention provides nucleic acids encoding a constant region of an antibody having amino acid alterations of the present invention. The nucleic acids encoding a constant region of the present invention may be in any form such as DNA or RNA.

Additionally, the present invention provides vectors comprising these nucleic acids. A vector type can be selected appropriately by those skilled in the art according to the host cell into which the vector will be introduced, and for example, a vector mentioned above can be used.

Furthermore, the present invention relates to host cells transformed with the vector. Host cells can be selected appropriately by those skilled in the art, and for example, the above-mentioned host cells may be used.

Moreover, the present invention relates to methods for producing the constant regions of the present invention, wherein the method comprises the steps of culturing the host cells and collecting the expressed constant regions.

<Methods for Enhancing Agonist Activity>

The present invention relates to methods for enhancing agonist activity by deleting or substituting at least one amino acid in the upper hinge region of a heavy chain in human IgG1 with other amino acids.

Furthermore, the present invention relates to methods for enhancing agonist activity of an agonistic antibody, comprising the step of deleting the amino acids in a human IgG constant region indicated below:
(a) deleting at least one amino acid selected from Lys at position 218, Ser at position 219, Asp at position 221, Lys at position 222, Thr at position 223, His at position 224, and Thr at position 225 (EU numbering).

In the above-mentioned method, the number of amino acids to be selected is not particularly limited, and 1, 2, 3, 4, 5, 6, or 7 amino acids can be selected from the above-mentioned amino acids.

In the present invention, preferred embodiments of a method for enhancing agonist activity include methods for enhancing the agonist activity of an agonistic antibody, comprising any of the steps of:
(i) deleting Thr at position 223, His at position 224, and Thr at position 225 (EU numbering);
(ii) deleting Lys at position 222, Thr at position 223, His at position 224, and Thr at position 225 (EU numbering);
(iii) deleting Asp at position 221, Lys at position 222, Thr at position 223, His at position 224, and Thr at position 225 (EU numbering); and
(iv) deleting Lys at position 218, Ser at position 219, Asp at position 221, Lys at position 222, Thr at position 223, His at position 224, and Thr at position 225 (EU numbering).

Furthermore, the present invention relates to a method for enhancing agonist activity, further comprising the step of any one of (1) to (8) below:
(1) substituting at least one amino acid selected from Ser at position 192, Leu at position 193, Ile at position 199, Lys at position 214, Pro at position 217, Ser at position 219, Cys at position 220, Asp at position 221, and Lys at position 222 (EU numbering) with other amino acids;
(2) substituting Ser at position 219 and Cys at position 220 with other amino acids;
(3) substituting Ser at position 219, Cys at position 220, Asp at position 221, and Lys at position 222 with other amino acids;
(4) substituting Lys at position 214, Pro at position 217, Ser at position 219, Cys at position 220, Asp at position 221, and Lys at position 222 (EU numbering) with other amino acids;
(5) substituting Lys at position 214, Ser at position 219, Cys at position 220, Asp at position 221, and Lys at position 222 (EU numbering) with other amino acids;
(6) substituting Ile at position 199, Lys at position 214, Pro at position 217, Ser at position 219, Cys at position 220, Asp at position 221, and Lys at position 222 (EU numbering) with other amino acids;
(7) substituting Ser at position 192, Leu at position 193, Ile at position 199, Lys at position 214, Pro at position 217, Ser at position 219, Cys at position 220, Asp at position 221, and Lys at position 222 (EU numbering) with other amino acids; and
(8) substituting Lys at position 214, Pro at position 217, Ser at position 219, and Cys at position 220 (EU numbering) with other amino acids
in the above-mentioned method for enhancing agonist activity comprising the step of (a) or any one of (i) to (iv).

The present invention also relates to methods for enhancing agonist activity of an agonistic antibody, which comprise the following steps of (a) deleting amino acids, and (b) substituting amino acids:
(a) deleting at least one amino acid selected from Thr at position 223, His at position 224, and Thr at position 225 (EU numbering); and
(b) substituting at least one amino acid selected from Lys at position 214, Pro at position 217, Ser at position 219, Cys at position 220, Asp at position 221, and Lys at position 222 (EU numbering) with other amino acids.

In the present invention, specific examples of methods for enhancing agonist activity include, for example, an invention optionally combining the above-described step of deleting amino acids of any one of (i) to (iv), with the above-described step of substituting amino acids of any one of (1) to (8) above. More specifically, examples include the following methods.

(1) A method for enhancing agonist activity of an agonistic antibody, comprising the steps of:
(a) deleting Thr at position 223, His at position 224, and Thr at position 225 (EU numbering); and
(b) substituting Ser at position 219 and Cys at position 220 (EU numbering) with other amino acids in the human IgG1 constant region.

(2) A method for enhancing agonist activity of an agonistic antibody, comprising the steps of:
(a) deleting Thr at position 223, His at position 224, and Thr at position 225 (EU numbering); and
(b) substituting Ser at position 219, Cys at position 220, Asp at position 221, and Lys at position 222 (EU numbering) with other amino acids in the human IgG1 constant region.

(3) A method for enhancing agonist activity of an agonistic antibody, comprising the steps of:
(a) deleting Thr at position 223, His at position 224, and Thr at position 225 (EU numbering); and
(b) substituting Lys at position 214, Pro at position 217, Ser at position 219, Cys at position 220, Asp at position 221, and Lys at position 222 (EU numbering) with other amino acids in the human IgG1 constant region.

(4) A method for enhancing agonist activity of an agonistic antibody, comprising the steps of:
(a) deleting Thr at position 223, His at position 224, and Thr at position 225 (EU numbering); and
(b) substituting Lys at position 214, Ser at position 219, Cys at position 220, Asp at position 221, and Lys at position 222 (EU numbering) with other amino acids in the human IgG1 constant region.

(5) A method for enhancing agonist activity of an agonistic antibody, comprising the steps of:
(a) deleting Thr at position 223, His at position 224, and Thr at position 225 (EU numbering); and
(b) substituting Ile at position 199, Lys at position 214, Pro at position 217, Ser at position 219, Cys at position 220, Asp at position 221, and Lys at position 222 (EU numbering) with other amino acids in the human IgG1 constant region.

(6) A method for enhancing agonist activity of an agonistic antibody, comprising the steps of:
(a) deleting Thr at position 223, His at position 224, and Thr at position 225 (EU numbering); and
(b) substituting Ser at position 192, Leu at position 193, Ile at position 199, Lys at position 214, Pro at position 217, Ser at position 219, Cys at position 220, Asp at position 221, and Lys at position 222 (EU numbering) with other amino acids in the human IgG1 constant region.

(7) A method for enhancing agonist activity of an agonistic antibody, comprising the steps of:
(a) deleting Asp at position 221, Lys at position 222, Thr at position 223, His at position 224, and Thr at position 225 (EU numbering); and
(b) substituting Lys at position 214, Pro at position 217, Ser at position 219, and Cys at position 220 (EU numbering) with other amino acids in the human IgG1 constant region.

While there is no limitation to the amino acids after substitution, preferably,

Ser at position 192 (EU numbering) is substituted with Asn;
Leu at position 193 (EU numbering) is substituted with Phe;
Ile at position 199 (EU numbering) is substituted with Thr;
Lys at position 214 (EU numbering) is substituted with Thr;
Pro at position 217 (EU numbering) is substituted with Arg;
Ser at position 219 (EU numbering) is substituted with Cys;
Cys at position 220 (EU numbering) is substituted with Ser;
Asp at position 221 (EU numbering) is substituted with Val; and
Lys at position 222 (EU numbering) is substituted with Glu.

The method of the present invention may include alterations (substitutions, deletions, additions, and/or insertions) or modifications of other amino acids, and other steps as long as the above-mentioned steps are included. Specific examples of alterations of other amino acids include, for example, deletion of Gly at position 446 (EU numbering) and/or Lys at position 447 (EU numbering), but are not limited thereto. Methods of altering and modifying amino acids are not particularly limited, but for example, they can be performed by the above-described site-directed mutagenesis methods, or methods described in the Examples. The order in which steps (a) and (b) are carried out does not matter.

Furthermore, the present invention provides methods for enhancing agonist activity by decreasing the flexibility of a constant region in human IgG1. In the present invention, decreasing the flexibility of a human IgG1 constant region means shortening the distance between two Fabs contained in an antibody, and/or decreasing the freedom of movement of the two Fabs contained in an antibody.

In the present invention, agonist activity means an activity that induces change in some kind of physiological activity upon binding of a ligand to a protein or such on the cell membrane such as a receptor, which leads to signal transduction and the like in the cell. Without limitation, examples of the physiological activity include proliferation activity, survival activity, differentiation activity, transcriptional activity, membrane transport activity, binding activity, proteolytic activity, phosphorylation/dephosphorylation activity, redox activity, transfer activity, nucleolytic activity, dehydration activity, cell death-inducing activity, and apoptosis-inducing activity.

Herein, there is no particular limitation to the protein on cell membrane, and it is possible to use any protein. Proteins on cell membrane include, for example, receptors, cancer antigens, MHC antigens, and differentiation antigens. The receptors include, for example, those belonging to the hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. Receptors belonging to these receptor families and their characteristics are described in various documents, for example, reviews such as Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234;

SAIBO KOGAKU (Cell Technology) Supplementary Volume Handbook Series "Secchaku Inshi Handbook (Handbook for Adhesion factors)" M. Miyasaka Ed. (1994) Shujunsha, Tokyo, Japan.

Specifically, receptors belonging to the above receptor families include, for example, human and mouse erythropoietin (EPO) receptors, human and mouse granulocyte colony stimulating factor (G-CSF) receptors, human and mouse thrombopoietin (TPO) receptors, human and mouse insulin receptors, human and mouse Flt-3 ligand receptors, human and mouse platelet-derived growth factor (PDGF) receptors, human and mouse interferon (IFN)-α and -β receptors, human and mouse leptin receptors, human and mouse growth hormone (GH) receptors, human and mouse interleukin (IL)-10 receptors, human and mouse insulin-like growth factor (IGF)-I receptors, human and mouse leukemia inhibitory factor (LIF) receptors, and human and mouse ciliary neurotrophic factor (CNTF) receptors (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFNα/βR: Uze, G. et al. (1990) Cell 60, 225-234; and Novick, D. et al. (1994) Cell 77, 391-400).

Cancer antigens are antigens expressed as cells become malignant, and are also called "tumor-specific antigens". Furthermore, abnormal sugar chains expressed on protein molecules or cell surface when the cells become cancerous are also cancer antigens, and are called "cancer-associated carbohydrate antigen". Such cancer antigens include, for example, CA19-9, CA15-3, and sialyl SSEA-1 (SLX).

MHC antigens are categorized into MHC class I and class II antigens. The MHC class I antigens include HLA-A, -B, -C, -E, -F, -G, and -H, while the MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, CDw130.

Any detection indicators for measuring changes in activity can be used as long as they can measure quantitative and/or qualitative changes. For example, indicators for cell free systems (cell free assays), cell-based systems (cell-based assays), tissue-based systems, or biological systems can be used.

Enzymatic reactions, as well as quantitative and/or qualitative changes in proteins, DNAs, or RNAs can be used as indicators for cell free systems. For enzymatic reactions, for example, amino acid transfer reaction, sugar transfer reaction, dehydration reaction, dehydrogenation reaction, substrate cleaving-reaction, and such can be used. Protein phosphorylation, dephosphorylation, dimerization, multimerization, degradation, dissociation, and such, and DNA or RNA amplification, cleavage, and elongation can also be used. For example, phosphorylation of a protein present in the downstream of a signal transduction pathway can be used as a detection indicator.

Cell phenotypic changes, for example, quantitative and/or qualitative changes of produced substances, change in proliferation activity, change in cell number, morphological change, and change in properties can be used as indicators for cell-based systems. Secretory proteins, surface antigens, intracellular proteins, mRNAs, and such can be used as produced substances. Formation of protrusions and/or change in the number of protrusions, change in flatness, change in the extent of elongation and/or in the horizontal to vertical ratio, change in cell size, change in internal structure, cell population heteromorphy/homogeneity, change in cell density, and such can be used as morphological changes. Such changes in morphology can be confirmed by microscopic observation. Anchorage dependency, cytokine-dependent responsiveness, hormone dependence, drug resistance, cell motility, cell migration activity, pulsatility, change in intracellular substances, and such can be used as changes in property. Cell motility includes cell infiltration activity and cell migration activity. Furthermore, for example, enzyme activity, mRNA level, amount of intracellular signaling substances such as $Ca^{2+}$ and cAMP, intracellular protein level, and such can be used as changes in intracellular substance. In the case of cell membrane receptors, changes in cell proliferation activity induced by receptor stimulation can be used as an indicator.

Functional changes based on the tissue used can be used as a detection indicator for tissue-based systems. Changes in tissue weight, hematologic changes such as change in the number of blood cells, changes in the protein level, enzyme activity, or amount of electrolytes, or changes in the circulatory system such as changes in blood pressure or heart rate can be used as indicators for biological systems.

Methods for measuring these detection indicators are not particularly limited, and absorbance, luminescence, coloring, fluorescence, radioactivity, fluorescence polarization degree, surface plasmon resonance signal, time-resolved fluorescence, mass, absorption spectrum, light scattering, fluorescence resonance energy transfer, and such can be used. These measurement methods are well known to those skilled in the art, and they can be suitably selected according to the purpose.

For example, absorption spectra can be measured with a commonly used photometer, plate reader, or such; luminescence can be measured with a luminometer or such; and fluorescence can be measured with a fluorometer or such. The mass can be measured using a mass spectrometer. Radioactivity can be measured using measurement instruments such as a gamma counter according to the type of radiation. The degree of fluorescence polarization can be measured using BEACON (TaKaRa), and surface plasmon resonance signals can be measured using BIACORE. Time-resolved fluorescence, fluorescence resonance energy transfer, and such can be measured using ARVO or such. Flow cytometers and such can also be used for the measurements. With regard to these measurement methods, two or more detection indicators may be measured using one measurement method, and if they are simple, multiple detection indicators can be measured by performing two or more measurements simultaneously and/or sequentially. For example, fluorescence and fluorescence resonance energy transfer can be measured simultaneously on a fluorometer.

In the present invention, agonist activity can be measured using methods known to those skilled in the art. For example, as described in the Examples, it is possible to determine by methods that measure agonist activity using cell proliferation as an indicator. More specifically, a substance to be measured for its agonist activity is added to cells that show agonist-dependent proliferation and the cells are cultured. Then, a reagent that exhibits a chromogenic reaction at a particular wavelength depending on the number of live cells is added and absorbance is measured. Then, agonist activity can be determined using the obtained absorbance as an indicator.

Cells showing agonist-dependent proliferation can also be prepared by methods known to those skilled in the art, and for example, when the protein on cell membrane is a receptor emitting cell proliferation signal, cells expressing this receptor can be used. When the protein on cell membrane is a receptor that does not emit any cell proliferation signal, a chimeric receptor comprising the intracellular region of a receptor emitting cell proliferation signal and the extracellular region of a receptor that does not emit any cell growth signal is prepared, and this chimeric receptor can be expressed in cells. Examples of a receptor that emits cell proliferation signal include the G-CSF receptor, mpl, neu, GM-CSF receptor, EPO receptor, c-kit, and FLT-3. Examples of cells that can be made to express the receptors include BaF3, NFS60, FDCP-1, FDCP-2, CTLL-2, DA-1, and KT-3.

<Pharmaceutical Compositions Comprising Antibodies>

The present invention provides pharmaceutical compositions comprising an antibody of the present invention.

The pharmaceutical compositions of the present invention can be formulated, in addition to the antibodies, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dose of the pharmaceutical composition containing an antibody or a polynucleotide encoding an antibody can be selected, for example, from the range of 0.0001 to 1,000 mg per kg of body weight. Alternatively, the dose may be, for example, in the range of 0.001 to 100,000 mg/patient. However, the dose is not limited to these values. The dose and method of administration vary depending on the patient's body weight, age, and symptoms, and can be appropriately selected by those skilled in the art.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Hereinbelow, the present invention is specifically described with reference to the Examples, but it is not to be construed as being limited thereto.

[Example 1] Acquisition of Mouse Anti-HLA-A Antibodies

Hybridoma Production
1.1 Preparation of Soluble HLA-A-Flag (sHLA-A-Flag) for Immunization
1.1.1 Construction of an sHLA-A Expression Vector and Production of an HLA-Producing CHO Line HLA-A-flag (SEQ ID NO: 1, 307-314 is a flag tag) which has a flag tag attached to the C terminus of the extracellular domain of HLA-A6802 (GenBank No. AM235885) was introduced into an animal cell expression vector. The nucleotide sequence was determined by a DNA sequencer, ABI PRISM 3700 DNA Sequencer (Applied Biosystems), using the BigDye Terminator Cycle Sequencing Kit (Applied Biosystems) according to the method described in the attached instructions. The produced expression vector was introduced into CHO cells to construct an HLA-producing CHO line.

1.1.2. Purification of sHLA-A-Flag

From the culture supernatant of CHO cells produced in 1.1.1, soluble HLA-Flag protein was purified using Q-Sepharose FF (GE Healthcare), ANTI-FLAG M2 Affinity Gel (SIGMA) and HiLoad 16/60 Superdex 200 pg (GE Healthcare). The gel-filtration-eluted fraction was concentrated using Centriprep YM-10 (Millipore), and then the protein concentration was calculated using the Dc Protein Assay Kit (BIO-RAD) by conversion to bovine gamma globulin.

1.2. Production of Mouse Anti-HLA-A Antibody-Producing Hybridomas 1.2.1. Production of Hybridomas using HLA-A Immunized Mice Four-week-old male MRL/lpr mice (Charles River Japan) were used for immunization.

In the initial immunization, the purified soluble HLA-A-FLAG (sHLA-flag) protein was prepared in complete adjuvant H37Ra (DIFCO #231131) at 100 µg/head for the number of mice used, and after producing an emulsion, 100 µL was used for each subcutaneous immunization. In the second immunization and thereafter, emulsions were produced using an incomplete adjuvant (DIFCO #263910), and 50 µg/head was used for immunization. Immunization was carried out every other week. After increase of serum antibody titer was confirmed, in the final immunization (the sixth immunization), sHLA-flag was adjusted to 50 µg/200 µL in PBS and this was administered intravenously to the mice at 200 µL/head.

Four days after the final immunization, mouse spleen cells and mouse myeloma cells P3X63Ag8U.1 (referred to as P3U1, ATCC CRL-1597) were subjected to cell fusion according to conventional methods using PEG1500 (Roche Diagnostics). Fused cells, more specifically hybridomas, were cultured in a HAT medium [RPMI1640+PS, 10% FCS, HAT (Sigma, H0262), 5% BM condimed H1 (Roche: #1088947)].

1.2.2. Selection of Hybridoma Cells

Approximately one week after fusion, primary screening was performed using cell aggregation-inducing activity as an indicator. For cell aggregation-inducing activity, ARH77 cells were seeded onto a 96-well plate at $2 \times 10^4$ cells/well/40 µL, 80 µL of culture supernatant of each hybridoma was added, and this was cultured at 37° C. for four hours. Each well was examined one by one under a microscope, and wells undergoing cell aggregation were determined by visual observation. Hybridoma cells in wells undergoing cell aggregation were selected as positive clones. Hybridoma cells in wells with positive cell aggregation-inducing activity were seeded again onto a 96-well plate at 2.5 cells/well, and after culturing for approximately ten days, the cell aggregation-inducing activity was investigated again. Secondary screening was performed using the antibody's cell death inducing activity as an indicator. ARH77 cells were seeded onto a 24-well plate at $1-8 \times 10^5$ cells/well, and the antibodies were added. They were cultured in 200 µL of medium at 37° C. for 4 to 5 hours or more. After collection in Eppendorf tubes, they were suspended in 100-200 µL of propidium iodide (PI) solution (5 µg/mL in FACS buffer), and incubated at room temperature for 15 minutes. Thereafter, the cells were precipitated by centrifugation, then suspended in 500 µL of FACS buffer, FACS (Beckman Coulter, ELITE) was performed to measure the proportion of PI-positive cells (dead cells), and cell death inducing activities of the clones were compared. As a result, clone F17B1 showing the strongest cell death inducing activity was selected.

[Example 2] Determination of the Variable Region of Mouse Anti-HLA-A Antibody F17B1

Total RNA was extracted from hybridoma cells using the RNeasy Mini Kit (QIAGEN), and cDNA was synthesized using the SMART RACE cDNA Amplification Kit (BD Biosciences). Using the prepared cDNA, the antibody variable region gene was inserted into a cloning vector by PCR. The nucleotide sequence of each DNA fragment was determined by a DNA sequencer, the ABI PRISM 3700 DNA Sequencer (Applied Biosystems), using the BigDye Terminator Cycle Sequencing Kit (Applied Biosystems) according to the method described in the attached instructions. The H-chain variable region is shown in SEQ ID NO: 2, and the L-chain variable region is shown in SEQ ID NO: 3 for the determined F17 mouse antibody. CDR and FR were determined according to Kabat numbering.

[Example 3] Acquisition of Humanized Anti-Human MHC Class I Antibody

The variable region of mouse F17B1 antibody was compared to the human germline sequence or human antibody sequence, and the FR sequence to be used for antibody humanization was determined. The FR sequences used are summarized in Table 1.

Humanized H-chain variable region H2 (SEQ ID NO: 4) is composed of FR1, FR2, FR3, and FR4 described in Table 1. H2_G1d (SEQ ID NO: 8) prepared by linking the prepared H2 with constant region G1d (SEQ ID NO: 6) was introduced into an animal cell expression vector.

Humanized L-chain variable region (SEQ ID NO: 5) is composed of FR1, FR2, FR3, and FR4 described in Table 1. FR3 is composed of two types of germline sequences hVk2_28; GVPDRFSGSGSGTDFTLKISRVEAEDVGVYYC (SEQ ID NO: 18) and Vk6_21; GVPSRFSGSGSGTDFTLTINSLEAEDAATYYC (SEQ ID NO: 19). L1_k0 (SEQ ID NO: 9) prepared by linking the prepared L1 with constant region k0 (SEQ ID NO: 7) was introduced into an animal cell expression vector.

Using the produced expression vector, H2_G1d/L1_k0 comprising H2_G1d (SEQ ID NO: 8) as the H chain and L1_k0 (SEQ ID NO: 9) as the L chain was produced. Expression and purification of antibodies were carried out by the method described in Reference Example 1.

TABLE 1

| H2 | REFERENTIAL SEQUENCE | HUMAN FR SEQUENCE | SEQ ID NO |
|---|---|---|---|
| FR1 | Accession No. U96288 | QVTLKESGPTLVKPTQTLTLTCAFSGFSLN | 10 |
| FR2 | Germline: hVH2_70 | WIRQPPGKALEWLA | 11 |
| FR3 | Accession No. AY393293 | RLTISKDSSKNQVDLTMTNMDPVDTATYYCAR | 12 |
| FR4 | Germline: JH1 | WGQGTLVTVSS | 13 |

TABLE 1-continued

| L1 | REFERENTIAL SEQUENCE | HUMAN FR SEQUENCE | SEQ ID NO |
|---|---|---|---|
| FR1 | Germline: hVk3_11 | EIVLTQSPATLSLSPGERATLSC | 14 |
| FR2 | Germline: hVk3_11 | WYQQKPGQAPRLLIY | 15 |
| FR3 | hVk228 + hVk6_21 | GVPDRFSGSGSGTDFTLTINSLEAEDAATYYC | 16 |
| FR4 | Germline: JK2 | FGQGTKLEIK | 17 |

[Example 4] Induction of Cell Death by Anti-Human MHC Class I Antibody H2-G1d_L1-k0

Human lymphoblastoma cell line IM-9 (ATCC, CCL-159) expressing human MHC class I was used. The cell death-inducing activity by anti-human MHC class I antibody H2-G1d_L1-k0 was measured as indicated below.

Purified H2-G1d_L1-k0 was adjusted to 20 μg/mL in a culture medium, and a total of nine serially diluted solutions (final concentration; 10-0.0015 μg/mL) were prepared at a dilution ratio of 3 using a 96 well U-bottom plate (BM Equipment). IM-9 cells were prepared in an RPMI1640 medium (SIGMA) containing 10% FBS (BOVOGEN), 2 mM L-glutamine, 1.5 g/L sodium bicarbonate, 4.5 g/L glucose, 10 mM HEPES, and 1 mM sodium pyruvate at $1.2 \times 10^5$ cells/mL. 50 μL of a cell suspension solution was seeded into 50 μL of diluted H2-G1d_L1-k0 solution, and this was cultured at 37° C. for three days in a 5% $CO_2$ incubator. After culturing, 10 μL of Cell Counting Kit-8 (Dojindo) was added to each well, and this was reacted at 37° C. for 4 hours in a 5% $CO_2$ incubator. Thereafter, absorbance (450 nm) was measured (Molecular Devices, Emax). The cell death-inducing activity of H2-G1d_L1-k0 was calculated as percentage (%) of inhibition by defining the value for the well containing only culture medium (without addition of cells or antibody) as 0% and the value for the well containing only the cells (without addition of antibody) as 100%. Measurements were performed at n=5 and their mean values were used. As a result, as shown in FIG. 1, H2-G1d_L1-k0 was found to suppress cell growth in a concentration-dependent manner in the IM9 cell line.

[Example 5] Effect of Enhancing Cell Death Activity by a Novel Constant Region M97

Several antibodies that bind to HLA class I and induce cell death activity are known (Rolf et al., The Journal of Immunology, 1996, 156: 1415-1424). These antibodies induce cell death by activating HLA class I. Similarly to these antibodies, the mouse antibody F17B1 is also predicted to be an agonistic antibody that induces cell death by activating HLA. Since many agonistic antibodies do not show activity by the Fab fragment alone, divalent binding and dimer formation are considered to be important. Furthermore, it has been reported that agonist activity increases when the molecular weight of antibodies that do not show sufficient activity as full-length antibodies is reduced to a form such as sc(Fv)2. Accordingly, the present inventors predicted that the distance between two Fabs is important for exhibiting agonist activity. The distance and mobility of the two Fabs differ among antibody subclasses. The hinge region has a great influence on the distance and mobility of two Fabs (EMBO J. 1988 July; 7(7): 1989-94, and Schneider W P et al. Proc Natl Acad Sci USA. 1988 April; 85(8): 2509-13).

Therefore, the present inventors considered altering the hinge region to enhance agonist activity.

In IgG1, the hinge region at EU numbering (see Sequences of proteins of immunological interest, NIH Publication No. 91-3242) 221-225 forms an open-turn helix (Marquart M et al. J Mol Biol. 1980 Aug. 25; 141(4): 369-91, and Ito W et al., Biochemistry. 1985 Nov. 5; 24(23): 6467-74). The Thr-His-Thr sequence in the amino acid sequence of 221-225 in IgG1 does not exist in IgG2 and IgG4 (Table 2). Therefore, the inventors focused on this sequence and decided to produce a novel constant region M97 (SEQ ID NO: 20) in which the Thr-His-Thr at 223-225 is deleted from G1d (SEQ ID NO: 6). To examine the effect of M97 on cell death activity, an expression vector of H2_M97 (SEQ ID NO: 21) was prepared according to the method of Reference Example 1. H2_M97/L1_k0 consisting of H2_M97 (SEQ ID NO: 21) as the H chain and L1_k0 (SEQ ID NO: 9) as the L chain was produced. The antibody was expressed and purified by the method described in Reference Example 1. The cell death activity of each of the produced antibodies was determined by the method described in Example 4.

Figure 2:
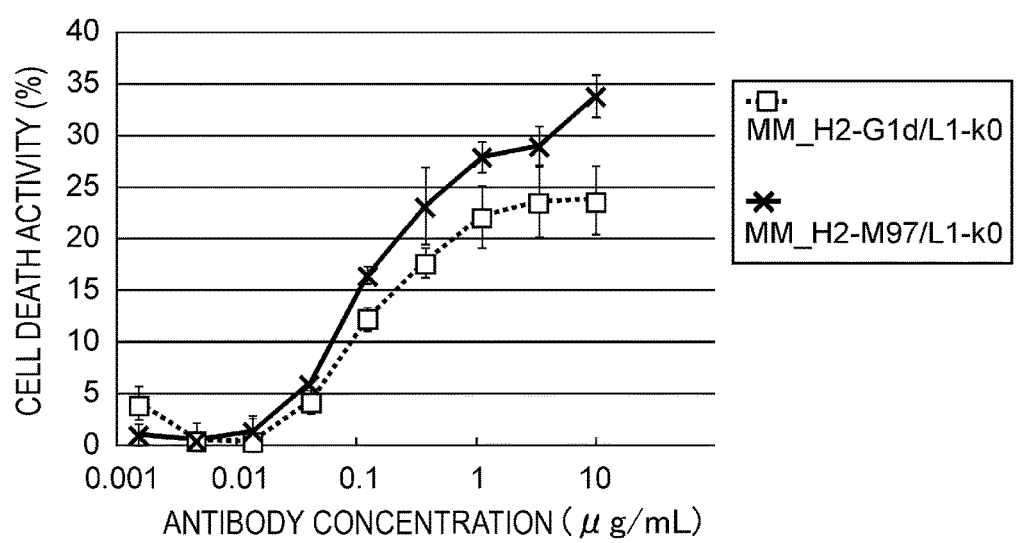
FIG. 2 presents a graph showing significant improvement of cell death activity by IgG1 when amino acid residues Thr-His-Thr (EU numbering 223-225) are deleted.

As shown in FIG. 2, deletion of Thr-His-Thr was confirmed to improve the cell death activity.

[Example 6] Activity-Enhancing Effect by Deletion of the Hinge Portion

In natural IgG1, Cys present at positions 226 and 229 form disulfide bonds with the other H chain. Furthermore, Cys at position 220 (EU numbering) in the H chain and Cys at position 214 (EU numbering) in the L chain form a disulfide bond. Five amino acids Asp-Lys-Thr-His-Thr present between Cys at position 220 and position 226 which form a disulfide bond. Since deletion of three of the five residues, the Thr-His-Thr sequence, improved the cell death activity, deletion of the remaining two residues, the Asp-Lys sequence, was considered to further improve cell death activity. Furthermore, since cell death activity is improved by shortening the hinge region, deletion of Lys at position 218 and Ser at position 219 was considered to further improve the cell death activity.

With regard to M97 (SEQ ID NO: 20), the inventors decided to produce constant region M167 (SEQ ID NO: 39) by deleting Lys at position 222 in the H chain; constant region M168 (SEQ ID NO: 40) by deleting Asp at position 221 and Lys at position 222 in the H chain; and constant region M169 (SEQ ID NO: 37) by deleting Lys at position 218, Ser at position 219, Asp at position 221, and Lys at position 222 in the H chain. The produced constant region sequences are summarized in Table 2.

Expression vectors for H2_M167 (SEQ ID NO: 43), H2_M168 (SEQ ID NO: 44), H2_M169 (SEQ ID NO: 41), and H2_M154 (SEQ ID NO: 42) were prepared according to the method of Reference Example 1. H2_M167/L1_k0 consisting of H2_M167 (SEQ ID NO: 43) was produced as the H chain and L1_k0 (SEQ ID NO: 9) as the L chain. H2_M168/L1_k0 consisting of H2_M168 (SEQ ID NO: 44) was produced as the H chain and L1_k0 (SEQ ID NO: 9) as the L chain. H2_M169/L1_k0 consisting of H2_M169 (SEQ ID NO: 41) was produced as the H chain and L1_k0 (SEQ ID NO: 9) as the L chain. The antibodies were expressed and purified by the method described in Reference Example 1. The cell death activity of each of the produced antibodies was determined by the method described in Example 4.

Combinations of the heavy chain and light chain of the above-mentioned antibodies are summarized below.

| Antibody | Heavy chain | Light chain |
|---|---|---|
| H2_M167/L1_k0 | H2_M167 SEQ ID NO: 43/ | L1-k0 SEQ ID NO: 9 |
| H2_M168/L1_k0 | H2_M168 SEQ ID NO: 44/ | L1-k0 SEQ ID NO: 9 |
| H2_M169/L1_k0 | H2_M169 SEQ ID NO: 41/ | L1-k0 SEQ ID NO: 9 |

Figure 3:
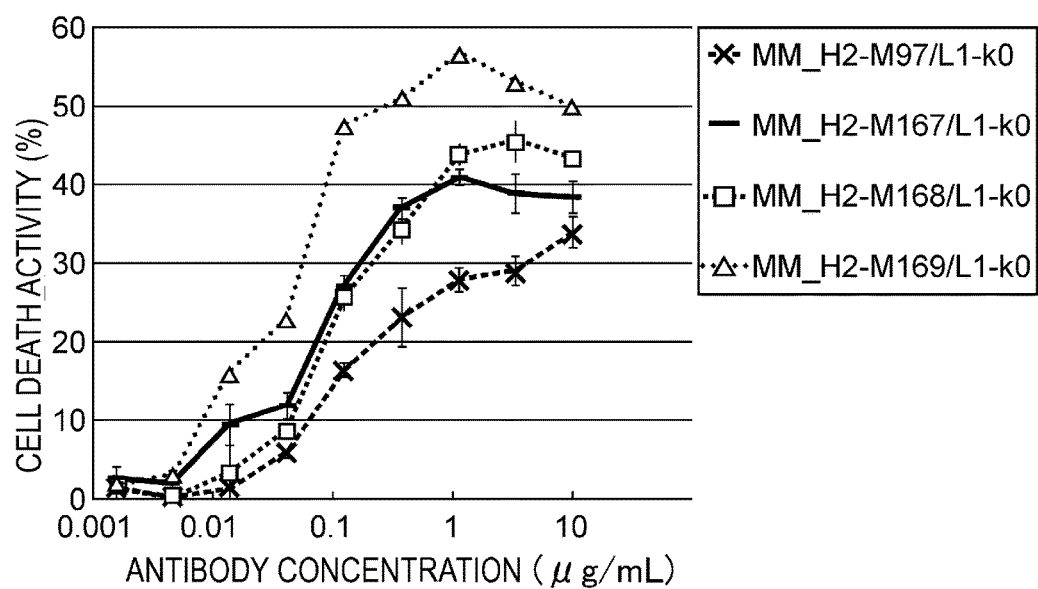
FIG. 3 presents a graph showing the cell death activity of antibodies containing constant regions M97, M167, M168, and M169.

As shown in FIG. 3, shortening the hinge region sequence showed an improving trend in cell death activity.

[Example 8] Effect of Enhancing Cell Death Activity by Novel Constant Regions M101, M132, M146, M148, and M152

Examples 5, 6, and 7 showed that cell death activity increases by altering the hinge region. Comparison of the hinge region sequences from each subclass reveals that the sequences are different depending on the subclass. Accordingly, the inventors decided to alter the hinge region sequence and the sequence around it to increase cell death activity.

In the upper hinge of the hinge region, other than the sequence of amino acids altered in Examples 5, 6, and 7, the amino acid sequence of Pro, Asp, and Lys at 217, 221, and 221 is different. Furthermore, of the amino acids present in the IgG1 CH1 domain, Ser, Leu, Ile, and Lys at 192, 193, 199, and 214 are present around the hinge region and different from the amino acid sequences of other subclasses. Thus, they are considered to have the possibility of influencing the hinge structure.

Accordingly, the inventors decided to produce M101 (SEQ ID NO: 24), M132 (SEQ ID NO: 26), M146 (SEQ ID NO: 45), M148 (SEQ ID NO: 33), and M152 (SEQ ID NO:

TABLE 2

```
                 190 1 2 3 4 5 6 7 8 9 200 1 2 3 4 5 6 7 8 9 210 1 2 3 4 5 6 7 8 9 220 1 2 3 4 5 6 7 8 9 230
(SEQ ID NO: 47)G1   S   S S L G T Q T Y I   C   N V N H K P S N T   K   V D K K V E P K S   C   D K T H T C P P C   P
(SEQ ID NO: 48)M97  -   - - - - - - - - -   -   - - - - - - - - -   -   - - - - - - - - -   -   - - / / - - - - -   -
(SEQ ID NO: 49)M167 -   - - - - - - - - -   -   - - - - - - - - -   -   - - - - - - - - -   -   - / / / / - - - -   -
(SEQ ID NO: 50)M168 -   - - - - - - - - -   -   - - - - - - - - -   -   - - - - - - - - -   -   / / / / / - - - -   -
(SEQ ID NO: 51)M169 -   - - - - - - - - -   -   - - - - - - - - -   -   - - - - - - - - -   / /   - / / / / / - - - -   -
```

/ MEANS THAT THERE IS NOT AN AMINO ACID.
- MEANS THAT AN AMINO ACID IS THE SAME AS THAT OF G1.

[Example 7] Effect of Enhancing Cell Death Activity by Substituting the Position of Cys In natural IgG1, Cys present at position 214 (EU numbering) in the L chain and Cys at position 220 (EU numbering) in the H chain form a disulfide bond (Saphire E O, et al. Science. 293, 1155-9 (2001)). For agonist activity, the distance between two Fabs and their structures are considered to be important, and the possibility of improving the activity by changing the disulfide bond between Cys at L chain position 214 and H chain was examined.

Accordingly, the inventors decided to produce a novel constant region M98 (SEQ ID NO: 22) prepared by substituting Cys at position 220 (EU numbering) and Ser at position 219 in the H chain of M97 (SEQ ID NO: 20) produced in Example 5 with Ser and Cys, respectively. An expression vector for H2_M98 (SEQ ID NO: 23) was prepared according to the method of Reference example 1 to examine the effect of M98 on cell death activity. H2_M98/L1_k0 consisting of H2_M98 (SEQ ID NO: 23) as the H chain and L1_k0 (SEQ ID NO: 9) as the L chain was produced. The antibody was expressed and purified by the method of Reference Example 1. The cell death activity of each of the produced antibodies was determined by the method described in Example 4.

Figure 4:
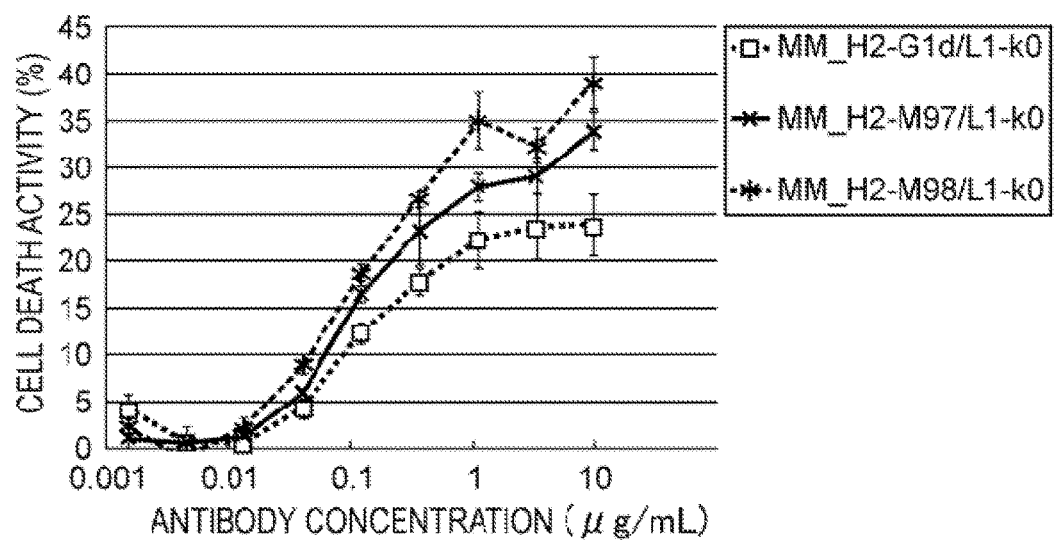
FIG. 4 presents a graph showing improvement of cell death activity depending on the position of Cys.

As shown in FIG. 4, changing the position of Cys was found to improve cell death activity.

34) which have substitutions in the amino acid sequence of IgG1. The sequences around the hinge region for each of the produced constant regions are summarized in Table 3. Expression vectors for H2_M101 (SEQ ID NO: 25), H2_M132 (SEQ ID NO: 27), H2_M146 (SEQ ID NO: 46), H2_M148 (SEQ ID NO: 35), and H2_M152 (SEQ ID NO: 36) were produced according to the method of Reference Example 1. H2_M101/L1_k0 consisting of H2_M101 (SEQ ID NO: 25) was produced as the H chain and L1_k0 (SEQ ID NO: 9) as the L chain. H2_M132/L1_k0 consisting of H2_M132 (SEQ ID NO: 27) was produced as the H chain and L1_k0 (SEQ ID NO: 9) as the L chain. H2_M146/L1_k0 consisting of H2_M146 (SEQ ID NO: 46) was produced as the H chain and L1_k0 (SEQ ID NO: 9) as the L chain. H2_M148/L1_k0 consisting of H2_M148 (SEQ ID NO: 35) was produced as the H chain and L1_k0 (SEQ ID NO: 9) as the L chain. H2_M152/L1_k0 consisting of H2_M152 (SEQ ID NO: 36) was produced as the H chain and L1_k0 (SEQ ID NO: 9) as the L chain. The antibodies were expressed and purified by the method of Reference Example 1. The cell death activity of each of the produced antibodies and that of H2_M97/L1_k0 produced in Example 5 were determined by the method described in Example 4.

Combinations of the heavy chain and light chain of the above-mentioned antibodies are summarized below.

| Antibody | Heavy chain | Light chain |
|---|---|---|
| H2_M101/L1_k0 | H2_M101 SEQ ID NO: 25/ | L1-k0 SEQ ID NO: 9 |
| H2_M132/L1_k0 | H2_M132 SEQ ID NO: 27/ | L1-k0 SEQ ID NO: 9 |
| H2_M146/L1_k0 | H2_M146 SEQ ID NO: 46/ | L1-k0 SEQ ID NO: 9 |
| H2_M148/L1_k0 | H2_M148 SEQ ID NO: 35/ | L1-k0 SEQ ID NO: 9 |
| H2_M152/L1_k0 | H2_M152 SEQ ID NO: 36/ | L1-k0 SEQ ID NO: 9 |

Figure 5:
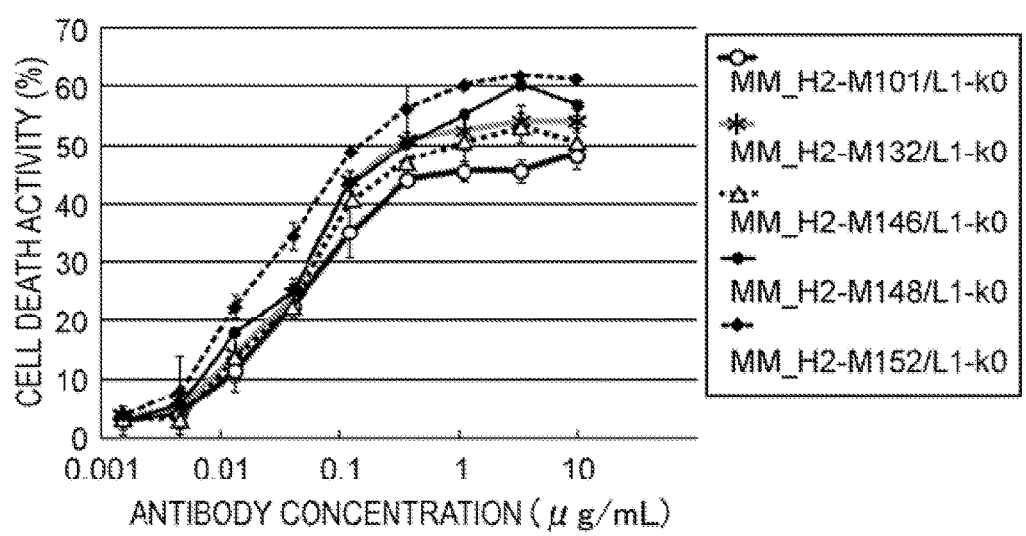
FIG. 5 presents a graph showing the cell death activity of antibodies containing constant regions M101, M132, M146, M148, and M152. M152, M148, M132, M146, and M101 are shown in order of increasing cell death activity.

As shown in FIG. 5, M152, M148, M132, M146, and M101 are shown in the order of strong activity.

TABLE 3

```
                  190 1 2 3 4 5 6 7 8 9 200 1 2 3 4 5 6 7 8 9 210 1 2 3 4 5 6 7 8 9 220 1 2 3 4 5 6 7 8 9 230

(SEQ ID NO: 47) G1    S S S L G T Q T Y I  C  N V N H K P S N T  K  V D K K V E P K S  C  D K T H T C P P C  P (SEQ ID NO: 48) M97   - - - - - - - - - -  -  - - - - - - - - -  -  - - - - - - - - -  -  - - / / / - - - -  -

(SEQ ID NO: 52) M98   - - - - - - - - - -  -  - - - - - - - - -  -  - - - - - - - - -  C  S - - / / / - - -  -

(SEQ ID NO: 53) M101  - - - - - - - - - -  -  - - - - - - - - -  -  - - - - - - - - -  C  S V E / / / - - -  -

(SEQ ID NO: 54) M132  - - - - - - - - - -  -  - - - - - - - - -  -  - - - T - - R - - -  C  S V E / / / - - -  -

(SEQ ID NO: 55) M146  - - - - - - - - - -  -  - - - - - - - - -  -  - - - T - - - - - -  C  S V E / / / - - -  -

(SEQ ID NO: 56) M148  - - - - - - - - T -  -  - - - - - - - - -  -  - - - T - - R - - -  C  S V E / / / - - -  -

(SEQ ID NO: 57) M152  - - - N F - - - - T  -  - - - - - - - - -  -  - - - T - - R - - -  C  S V E / / / - - -  -
```

/ MEANS THAT THERE IS NOT AN AMINO ACID.
— MEANS THAT AN AMINO ACID IS THE SAME AS THAT OF G1.

[Example 9] Enhancing Effect on Cell Death Activity by the Novel Constant Regions M133 and M134

Use of a mouse constant region has elucidated that not only the upper hinge composed of EU numbering 216-225, but also the lower hinge composed of 231-238 affects the structure of the constant region (Kim H et al. J Mol. Biol. 1994 Feb. 11; 236(1): 300-9). Accordingly, the inventors decided to produce M133 (SEQ ID NO: 28) and M134 (SEQ ID NO: 30) prepared by substituting the lower hinge of M101 (SEQ ID NO: 24) and M132 (SEQ ID NO: 26) with the lower hinge of IgG2.

Expression vectors for H2_M133 (SEQ ID NO: 29) and H2_M134 (SEQ ID NO: 31) were produced according to the method of Reference Example 1. H2_M133/L1_k0 consisting of H2_M133 (SEQ ID NO: 29) was produced as the H chain and L1_k0 (SEQ ID NO: 9) as the L chain. H2_M134/L1_k0 consisting of H2_M134 (SEQ ID NO: 31) was produced as the H chain and L1_k0 (SEQ ID NO: 9) as the L chain. The antibodies were expressed and purified by the method described in Reference Example 1. The cell death activity of each of the produced antibodies and that of H2_M97/L1_k0 produced in Example 5 were determined by the method described in Example 4.

Combinations of the heavy chain and light chain of the above-mentioned antibodies are summarized below.

| Antibody | Heavy chain | Light chain |
|---|---|---|
| H2_M133/L1_k0 | H2_M133 SEQ ID NO: 29/ | L1-k0 SEQ ID NO: 9 |
| H2_M134/L1_k0 | H2_M134 SEQ ID NO: 31/ | L1-k0 SEQ ID NO: 9 |

Figure 6:
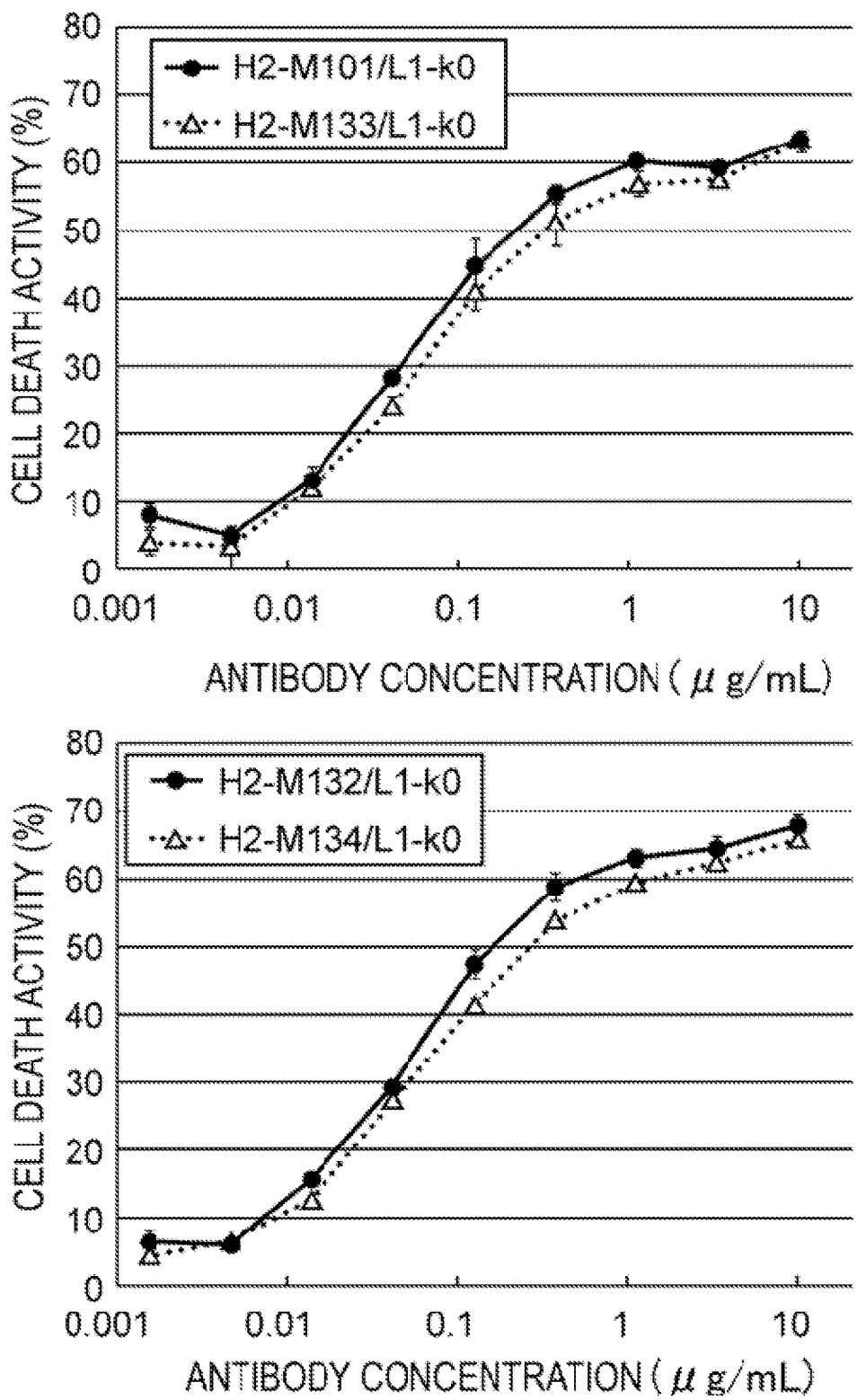
FIG. 6 presents a pair of graphs showing the cell death activity of antibodies containing constant regions M133 and M101 (top graph), and M134 and M132 (bottom graph).

As shown in FIG. 6, a decreasing trend of cell death activity was shown by substituting the lower hinge of IgG1 with that of IgG2. Not the lower hinge but the upper hinge was shown to be important for cell death activity.

[Example 10] Activity Enhancing Effect by Deletion of the Hinge Region in the Novel Constant Region M132

To confirm and verify the activity-enhancing effect as a result of deleting the hinge in H2-M132/L1-k0 produced in Example 8, the inventors decided to produce constant region M154 (SEQ ID NO: 38) prepared by deleting Asp at position 221 and Lys at position 222 in the H chain of M132 (SEQ ID NO: 26). H2_M154/L1_k0 consisting of H2_M154 (SEQ ID NO: 42) was produced as the H chain and L1_k0 (SEQ ID NO: 9) as the L chain.

| Antibody | Heavy chain | Light chain |
|---|---|---|
| H2_M132/L1_k0 | H2_M132 SEQ ID NO: 27/ | L1-k0 SEQ ID NO: 9 |
| H2_M154/L1_k0 | H2_M154 SEQ ID NO: 42/ | L1-k0 SEQ ID NO: 9 |

Figure 7:
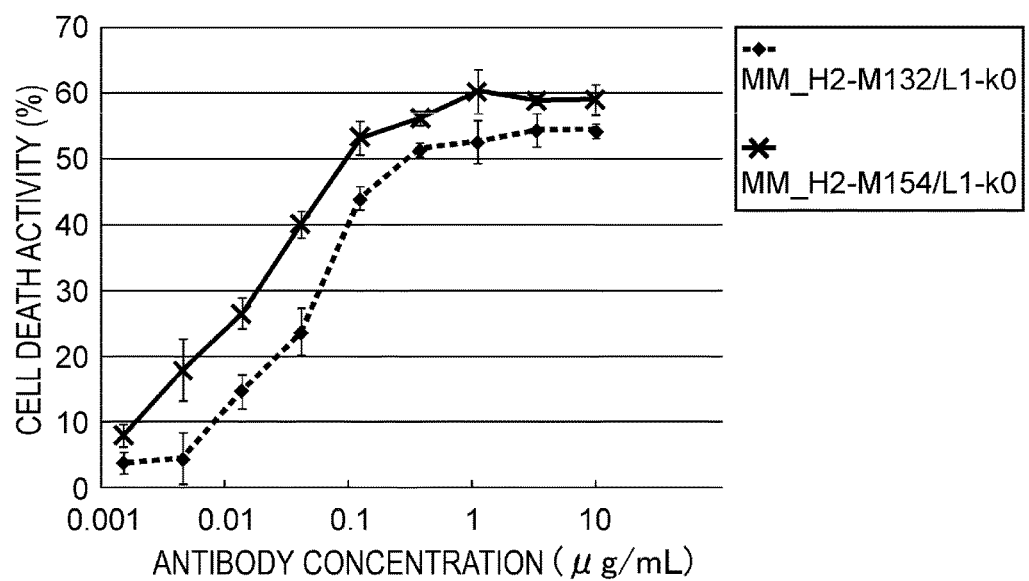
FIG. 7 presents a graph showing the cell death activity of antibodies containing constant regions M132 and M154.

As shown in FIG. 7, an improving trend of cell death activity was shown by shortening the hinge region sequence. Accordingly, deletion of the hinge site was found to improve activity not only in IgG1 but also in the constant regions produced by altering IgG1.

TABLE 4

| | | 190 | 191 | 192 | 193 | 194 | 195 | 196 | 197 | 198 | 199 | 200 | 201 | 202 | 203 | 204 | 205 | 206 | 207 | 208 | 209 | 210 | 211 | 212 | 213 | 214 | 215 | 216 | 217 | 218 | 219 | 220 | 221 | 222 | 223 | 224 | 225 | 226 | 227 | 228 | 229 | 230 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| (SEQ ID NO: 47) | G1 | S | S | S | L | G | T | Q | T | Y | I | C | N | V | N | H | K | P | S | N | T | K | V | D | K | K | V | E | P | K | S | C | D | K | T | H | T | C | P | P | C | P |
| (SEQ ID NO: 54) | M132 | – | – | – | – | – | – | – | – | – | – | – | – | – | – | – | – | – | – | – | – | – | – | – | – | T | – | – | R | – | C | S | V | E | / | / | / | – | – | – | – | – |
| (SEQ ID NO: 58) | M154 | – | – | – | – | – | – | – | – | – | – | – | – | – | – | – | – | – | – | – | – | – | – | – | – | T | – | – | R | – | C | S | / | / | / | / | / | – | – | – | – | – |

/ MEANS THAT THERE IS NOT AN AMINO ACID.
– MEANS THAT AN AMINO ACID IS THE SAME AS THAT OF G1.

Reference: Saphire, E. O. et al. Science 293 (5532), 1155-1159

[Reference Example 1] Production of Antibody Expression Vectors, and Expression and Purification of Antibodies Genes encoding the nucleotide sequences of the H chain and L chain of the antibody of interest were amplified using Assemble PCR and such by methods known to those skilled in the art. Introduction of amino acid substitutions was carried out by methods known to those skilled in the art using the QuikChange Site-Directed Mutagenesis Kit (Stratagene), PCR, or such. The obtained plasmid fragment was inserted into an animal cell expression vector, and the H-chain expression vector and L-chain expression vector of interest were produced. The nucleotide sequence of the obtained expression vector was determined by a method known to those skilled in the art. The antibodies were expressed by the following method. Human embryonic kidney cancer-derived HEK293H cells (Invitrogen) were suspended in DMEM (Invitrogen) supplemented with 10% Fetal Bovine Serum (Invitrogen). The cells (10-ml/plate; cell density of 5 to $6 \times 10^5$ cells/ml) were plated on dishes for adherent cells (10 cm in diameter; CORNING) and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmids were introduced into cells by the lipofection method. The resulting culture supernatants were collected and centrifuged (approx. 2,000 g, 5 min, room temperature) to remove the cells, and sterilized through 0.22-μm filter MILLEX®-GV (Millipore). Antibodies were purified from the obtained culture supernatant by a method known to those skilled in the art using rProtein A Sepharose™ Fast Flow (Amersham Biosciences). Absorbance at 280 nm was measured using a spectrophotometer to know the purified antibody concentrations. Extinction coefficient calculated from the obtained value by the PACE method was used to calculate the antibody concentration (Protein Science 1995; 4: 2411-2423).

INDUSTRIAL APPLICABILITY

The antibody constant regions of the present invention are useful as constant regions of antibodies administered to living organisms as pharmaceuticals. Agonist activity is enhanced in antibodies containing a constant region of the present invention. Therefore, antibodies comprising a constant region of the present invention can contribute to improvement of the performance of pharmaceutical products.

The invention claimed is:

1. An antibody comprising a heavy chain and a light chain that together comprise a Fab fragment that binds to a target antigen, wherein the antibody agonizes the target antigen, and wherein the heavy chain comprises a constant region that comprises the amino acid sequence of SEQ ID NO: 32 with only the following mutations, wherein all positions are identified by EU numbering:
   (a) deletion of the amino acid residues at positions 222, 223, 224, and 225; and
   (b) optionally, one of the following (1) to (3):
   (1) substitution of the amino acid residues at positions 219 and 220 with Cys and Ser, respectively;
   (2) substitution of the amino acid residues at positions 219, 220, and 221 with Cys, Ser, and Val, respectively; or
   (3) substitution of the amino acid residues at positions 192, 193, 199, 214, 217, 219, 220, and 221 with Asn, Phe, Thr, Thr, Arg, Cys, Ser, and Val, respectively.

2. The antibody of claim 1, wherein the heavy chain comprises a constant region that comprises the amino acid sequence of SEQ ID NO: 32 with only the following mutations, wherein all positions are identified by EU numbering:
   (a) deletion of the amino acid residues at positions 222, 223, 224, and 225.

3. The antibody of claim 1, wherein the mutations include substitution of the amino acid residues at EU numbering positions 219 and 220 with Cys and Ser, respectively.

4. The antibody of claim 1, wherein the mutations include substitution of the amino acid residues at EU numbering positions 219, 220, and 221 with Cys, Ser, and Val, respectively.

5. The antibody of claim 1, wherein the mutations include substitution of the amino acid residues at EU numbering positions 192, 193, 199, 214, 217, 219, 220, and 221 with Asn, Phe, Thr, Thr, Arg, Cys, Ser, and Val, respectively.

* * * * *

SEQUENCE LISTING

```
<160> NUMBER OF SEQ ID NOS: 58

<210> SEQ ID NO 1
<211> LENGTH: 314
<212> TYPE: PRT
<213> ORGANISM: Artificial
<220> FEATURE:
<223> OTHER INFORMATION: An artificially synthesized peptide sequence
<220> FEATURE:
<221> NAME/KEY: VARIANT
<222> LOCATION: (307)..(314)
<223> OTHER INFORMATION: flag tag

<400> SEQUENCE: 1

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Tyr Thr Ser Met Ser Arg Pro Gly Arg Gly Glu Pro Arg Phe Ile Ala
        35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80
```

```
Pro Glu Tyr Trp Asp Arg Asn Thr Arg Asn Val Lys Ala Gln Ser Gln
                85                  90                  95

Thr Asp Arg Val Asp Leu Gly Thr Leu Arg Gly Tyr Tyr Asn Gln Ser
            100                 105                 110

Glu Ala Gly Ser His Thr Ile Gln Arg Met Tyr Gly Cys Asp Val Gly
        115                 120                 125

Pro Asp Gly Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Trp Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Val Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Asp Tyr Lys Asp Asp Asp Lys
305                 310

<210> SEQ ID NO 2
<211> LENGTH: 129
<212> TYPE: PRT
<213> ORGANISM: Mus musculus

<400> SEQUENCE: 2

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Phe
            20                  25                  30

Asn Met Gly Ile Gly Trp Ile Arg Gln Pro Ser Gly Lys Gly Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ala
        115                 120                 125

Ala
```

<210> SEQ ID NO 3
<211> LENGTH: 111
<212> TYPE: PRT
<213> ORGANISM: Mus musculus

<400> SEQUENCE: 3

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile Arg
            20                  25                  30

Gly Thr Ser Leu Met His Trp Tyr Gln Gln Lys Pro Gly Tyr Ala Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Ser Arg
                85                  90                  95

Glu Tyr Pro Tyr Thr Phe Gly Ser Gly Thr Lys Leu Glu Ile Lys
            100                 105                 110
```

<210> SEQ ID NO 4
<211> LENGTH: 128
<212> TYPE: PRT
<213> ORGANISM: Artificial
<220> FEATURE:
<223> OTHER INFORMATION: An artificially synthesized peptide sequence

<400> SEQUENCE: 4

```
Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125
```

<210> SEQ ID NO 5
<211> LENGTH: 111
<212> TYPE: PRT
<213> ORGANISM: Artificial
<220> FEATURE:
<223> OTHER INFORMATION: An artificially synthesized peptide sequence

<400> SEQUENCE: 5

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ile Arg
            20                  25                  30
```

```
Gly Thr Ser Leu Met His Trp Tyr Gln Gln Lys Pro Gly Gln Ala Pro
            35                  40                  45

Arg Leu Leu Ile Tyr Arg Ala Ser Asn Leu Glu Ser Gly Val Pro Asp
 50                  55                  60

Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys Gln Gln Ser Arg
                85                  90                  95

Glu Tyr Pro Tyr Thr Phe Gly Gln Gly Thr Lys Leu Glu Ile Lys
                100                 105                 110

<210> SEQ ID NO 6
<211> LENGTH: 328
<212> TYPE: PRT
<213> ORGANISM: Homo sapiens

<400> SEQUENCE: 6

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 8
<211> LENGTH: 456
<212> TYPE: PRT
<213> ORGANISM: Artificial
<220> FEATURE:
<223> OTHER INFORMATION: An artificially synthesized peptide sequence

<400> SEQUENCE: 8

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175
```

```
Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro
    450                 455

<210> SEQ ID NO 9
<211> LENGTH: 218
<212> TYPE: PRT
<213> ORGANISM: Artificial
<220> FEATURE:
<223> OTHER INFORMATION: An artificially synthesized peptide sequence

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Ile Arg
            20                  25                  30

Gly Thr Ser Leu Met His Trp Tyr Gln Gln Lys Pro Gly Gln Ala Pro
        35                  40                  45

Arg Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Asn
65                  70                  75                  80
```

```
Ser Leu Glu Ala Glu Asp Ala Thr Tyr Tyr Cys Gln Gln Ser Arg
                85                  90                  95

Glu Tyr Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

<210> SEQ ID NO 10
<211> LENGTH: 30
<212> TYPE: PRT
<213> ORGANISM: Homo sapiens

<400> SEQUENCE: 10

```
Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn
            20                  25                  30
```

<210> SEQ ID NO 11
<211> LENGTH: 14
<212> TYPE: PRT
<213> ORGANISM: Homo sapiens

<400> SEQUENCE: 11

```
Trp Ile Arg Gln Pro Pro Gly Lys Ala Leu Glu Trp Leu Ala
1               5                   10
```

<210> SEQ ID NO 12
<211> LENGTH: 32
<212> TYPE: PRT
<213> ORGANISM: Homo sapiens

<400> SEQUENCE: 12

```
Arg Leu Thr Ile Ser Lys Asp Ser Ser Lys Asn Gln Val Asp Leu Thr
1               5                   10                  15

Met Thr Asn Met Asp Pro Val Asp Thr Ala Thr Tyr Tyr Cys Ala Arg
            20                  25                  30
```

<210> SEQ ID NO 13
<211> LENGTH: 11
<212> TYPE: PRT
<213> ORGANISM: Homo sapiens

<400> SEQUENCE: 13

```
Trp Gly Gln Gly Thr Leu Val Thr Val Ser Ser
1               5                   10
```

<210> SEQ ID NO 14

```
<211> LENGTH: 23
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 15
<211> LENGTH: 15
<212> TYPE: PRT
<213> ORGANISM: Homo sapiens

<400> SEQUENCE: 15

Trp Tyr Gln Gln Lys Pro Gly Gln Ala Pro Arg Leu Leu Ile Tyr
1               5                   10                  15

<210> SEQ ID NO 16
<211> LENGTH: 32
<212> TYPE: PRT
<213> ORGANISM: Homo sapiens

<400> SEQUENCE: 16

Gly Val Pro Asp Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 17
<211> LENGTH: 10
<212> TYPE: PRT
<213> ORGANISM: Homo sapiens

<400> SEQUENCE: 17

Phe Gly Gln Gly Thr Lys Leu Glu Ile Lys
1               5                   10

<210> SEQ ID NO 18
<211> LENGTH: 32
<212> TYPE: PRT
<213> ORGANISM: Homo sapiens

<400> SEQUENCE: 18

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 19
<211> LENGTH: 32
<212> TYPE: PRT
<213> ORGANISM: Homo sapiens

<400> SEQUENCE: 19

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 20
<211> LENGTH: 325
```

<212> TYPE: PRT
<213> ORGANISM: Artificial
<220> FEATURE:
<223> OTHER INFORMATION: An artificially synthesized peptide sequence

<400> SEQUENCE: 20

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Cys Pro Pro Cys Pro Ala Pro
            100                 105                 110
Glu Leu Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
130                 135                 140
Asp Val Ser His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Ala Leu
        195                 200                 205
Pro Ala Pro Ile Glu Lys Thr Ile Ser Lys Ala Lys Gly Gln Pro Arg
    210                 215                 220
Glu Pro Gln Val Tyr Thr Leu Pro Pro Ser Arg Asp Glu Leu Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Lys Leu Thr Val Asp Lys Ser Arg Trp Gln Gln Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Pro
                325

<210> SEQ ID NO 21
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 21

```
Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr Tyr His Pro Ser
50                      55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Lys Val Glu Pro Lys Ser Cys Asp Lys Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

```
Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro
    450
```

<210> SEQ ID NO 22
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 22

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Cys Ser Asp Lys Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Pro
            325

<210> SEQ ID NO 23
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 23

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Cys Ser Asp Lys Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

```
Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro
    450

<210> SEQ ID NO 24
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Cys Ser Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 25
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 25

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
            85                  90                  95

Cys Ala Arg Ile Val Gly Glu Arg Ala Tyr Tyr Ser Asn Tyr Gly Phe
        100                 105                 110

Ala Trp Phe Thr Tyr Trp Gly Gln Gly Thr Leu Val Thr Val Ser Ser
    115                 120                 125

Ala Ser Thr Lys Gly Pro Ser Val Phe Pro Leu Ala Pro Ser Ser Lys
            130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
    195                 200                 205

Tyr Ile Cys Asn Val Asn His Lys Pro Ser Asn Thr Lys Val Asp Lys
210                 215                 220

Lys Val Glu Pro Lys Cys Ser Val Glu Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
    275                 280                 285
```

-continued

```
Gly Val Glu Val His Asn Ala Lys Thr Lys Pro Arg Glu Glu Gln Tyr
            290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
        355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
        435                 440                 445
Leu Ser Leu Ser Pro
450

<210> SEQ ID NO 26
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 26

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Thr Val Glu Arg Lys Cys Ser Val Glu Cys Pro Pro Cys Pro Ala Pro
            100                 105                 110
Glu Leu Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser His Glu Asp Pro Glu Val Lys Phe Asn Trp Tyr Val Asp
145                 150                 155                 160
Gly Val Glu Val His Asn Ala Lys Thr Lys Pro Arg Glu Glu Gln Tyr
                165                 170                 175
Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 27
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 27

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220
```

```
Thr Val Glu Arg Lys Cys Ser Val Glu Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro
            450

<210> SEQ ID NO 28
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Val Asp
            130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 29
<211> LENGTH: 452
<212> TYPE: PRT
<213> ORGANISM: Artificial
<220> FEATURE:
<223> OTHER INFORMATION: An artificially synthesized peptide sequence

<400> SEQUENCE: 29

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
```

```
            165                 170                 175
Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
            195                 200                 205

Tyr Ile Cys Asn Val Asn His Lys Pro Ser Asn Thr Lys Val Asp Lys
            210                 215                 220

Lys Val Glu Pro Lys Cys Ser Val Glu Cys Pro Pro Cys Pro Ala Pro
225                 230                 235                 240

Pro Val Ala Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro
            450

<210> SEQ ID NO 30
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Thr Val Glu Arg Lys Cys Ser Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 31
<211> LENGTH: 452
<212> TYPE: PRT
<213> ORGANISM: Artificial
<220> FEATURE:
<223> OTHER INFORMATION: An artificially synthesized peptide sequence

<400> SEQUENCE: 31

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
                100                 105                 110
```

```
Ala Trp Phe Thr Tyr Trp Gly Gln Gly Thr Leu Val Thr Val Ser Ser
            115                 120                 125
Ala Ser Thr Lys Gly Pro Ser Val Phe Pro Leu Ala Pro Ser Ser Lys
        130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
    210                 215                 220
Thr Val Glu Arg Lys Cys Ser Val Glu Cys Pro Pro Cys Pro Ala Pro
225                 230                 235                 240
Pro Val Ala Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro
    450

<210> SEQ ID NO 32
<211> LENGTH: 330
<212> TYPE: PRT
<213> ORGANISM: Homo sapiens

<400> SEQUENCE: 32

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
```

```
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 33
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 33

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
```

```
              50                  55                  60
Leu Ser Ser Val Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Thr Val Glu Arg Lys Cys Ser Val Glu Cys Pro Pro Cys Pro Ala Pro
                100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro
            325

<210> SEQ ID NO 34
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 34

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asn His Lys Pro Ser Asn Thr Lys Val Asp Lys
```

```
                85                  90                  95
Thr Val Glu Arg Lys Cys Ser Val Glu Cys Pro Pro Cys Pro Ala Pro
                100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 35
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 35

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
                100                 105                 110

Ala Trp Phe Thr Tyr Trp Gly Gln Gly Thr Leu Val Thr Val Ser Ser
```

```
            115                 120                 125
Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Thr Cys Asn Val Asn His Lys Pro Ser Asn Thr Lys Val Asp Lys
    210                 215                 220

Thr Val Glu Arg Lys Cys Ser Val Glu Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450

<210> SEQ ID NO 36
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 36

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
```

-continued

Asn Met Gly Ile Gly Trp Ile Arg Gln Pro Pro Gly Lys Ala Leu Glu
            20                  25                  30
                35                      40                      45
Trp Leu Ala His Ile Trp Trp Asn Asp Asp Tyr Tyr Tyr His Pro Ser
        50                      55                      60
Leu Lys Ser Arg Leu Thr Ile Ser Lys Asp Ser Ser Lys Asn Gln Val
65                      70                      75                      80
Asp Leu Thr Met Thr Asn Met Asp Pro Val Asp Thr Ala Thr Tyr Tyr
                85                      90                      95
Cys Ala Arg Ile Val Gly Glu Arg Ala Tyr Tyr Ser Asn Tyr Gly Phe
            100                     105                     110
Ala Trp Phe Thr Tyr Trp Gly Gln Gly Thr Leu Val Thr Val Ser Ser
            115                     120                     125
Ala Ser Thr Lys Gly Pro Ser Val Phe Pro Leu Ala Pro Ser Ser Lys
            130                     135                     140
Ser Thr Ser Gly Gly Thr Ala Ala Leu Gly Cys Leu Val Lys Asp Tyr
145                     150                     155                     160
Phe Pro Glu Pro Val Thr Val Ser Trp Asn Ser Gly Ala Leu Thr Ser
                165                     170                     175
Gly Val His Thr Phe Pro Ala Val Leu Gln Ser Ser Gly Leu Tyr Ser
            180                     185                     190
Leu Ser Ser Val Val Thr Val Pro Ser Ser Asn Phe Gly Thr Gln Thr
            195                     200                     205
Tyr Thr Cys Asn Val Asn His Lys Pro Ser Asn Thr Lys Val Asp Lys
            210                     215                     220
Thr Val Glu Arg Lys Cys Ser Val Glu Cys Pro Pro Cys Pro Ala Pro
225                     230                     235                     240
Glu Leu Leu Gly Gly Pro Ser Val Phe Leu Phe Pro Pro Lys Pro Lys
                245                     250                     255
Asp Thr Leu Met Ile Ser Arg Thr Pro Glu Val Thr Cys Val Val Val
            260                     265                     270
Asp Val Ser His Glu Asp Pro Glu Val Lys Phe Asn Trp Tyr Val Asp
            275                     280                     285
Gly Val Glu Val His Asn Ala Lys Thr Lys Pro Arg Glu Glu Gln Tyr
            290                     295                     300
Asn Ser Thr Tyr Arg Val Val Ser Val Leu Thr Val Leu His Gln Asp
305                     310                     315                     320
Trp Leu Asn Gly Lys Glu Tyr Lys Cys Lys Val Ser Asn Lys Ala Leu
                325                     330                     335
Pro Ala Pro Ile Glu Lys Thr Ile Ser Lys Ala Lys Gly Gln Pro Arg
            340                     345                     350
Glu Pro Gln Val Tyr Thr Leu Pro Pro Ser Arg Asp Glu Leu Thr Lys
            355                     360                     365
Asn Gln Val Ser Leu Thr Cys Leu Val Lys Gly Phe Tyr Pro Ser Asp
            370                     375                     380
Ile Ala Val Glu Trp Glu Ser Asn Gly Gln Pro Glu Asn Asn Tyr Lys
385                     390                     395                     400
Thr Thr Pro Pro Val Leu Asp Ser Asp Gly Ser Phe Phe Leu Tyr Ser
                405                     410                     415
Lys Leu Thr Val Asp Lys Ser Arg Trp Gln Gln Gly Asn Val Phe Ser
            420                     425                     430
Cys Ser Val Met His Glu Ala Leu His Asn His Tyr Thr Gln Lys Ser
            435                     440                     445

```
Leu Ser Leu Ser Pro
    450

<210> SEQ ID NO 37
<211> LENGTH: 321
<212> TYPE: PRT
<213> ORGANISM: Artificial
<220> FEATURE:
<223> OTHER INFORMATION: An artificially synthesized peptide sequence

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Cys Cys Pro Pro Cys Pro Ala Pro Glu Leu Leu Gly
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
    130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Arg Asp Glu Leu Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300

His Glu Ala Leu His Asn His Tyr Thr Gln Lys Ser Leu Ser Leu Ser
305                 310                 315                 320

Pro

<210> SEQ ID NO 38
<211> LENGTH: 323
```

```
<212> TYPE: PRT
<213> ORGANISM: Artificial
<220> FEATURE:
<223> OTHER INFORMATION: An artificially synthesized peptide sequence

<400> SEQUENCE: 38
```

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | 55 | | | | | 60 | | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Thr | Val | Glu | Arg | Lys | Cys | Ser | Cys | Pro | Cys | Pro | Ala | Pro | Glu | Leu |
| | | | 100 | | | | | 105 | | | | | 110 | | |
| Leu | Gly | Gly | Pro | Ser | Val | Phe | Leu | Phe | Pro | Pro | Lys | Pro | Lys | Asp | Thr |
| | | | 115 | | | | | 120 | | | | | 125 | | |
| Leu | Met | Ile | Ser | Arg | Thr | Pro | Glu | Val | Thr | Cys | Val | Val | Val | Asp | Val |
| 130 | | | | | 135 | | | | | 140 | | | | | |
| Ser | His | Glu | Asp | Pro | Glu | Val | Lys | Phe | Asn | Trp | Tyr | Val | Asp | Gly | Val |
| 145 | | | | | 150 | | | | | 155 | | | | | 160 |
| Glu | Val | His | Asn | Ala | Lys | Thr | Lys | Pro | Arg | Glu | Glu | Gln | Tyr | Asn | Ser |
| | | | | 165 | | | | | 170 | | | | | 175 | |
| Thr | Tyr | Arg | Val | Val | Ser | Val | Leu | Thr | Val | Leu | His | Gln | Asp | Trp | Leu |
| | | | 180 | | | | | 185 | | | | | 190 | | |
| Asn | Gly | Lys | Glu | Tyr | Lys | Cys | Lys | Val | Ser | Asn | Lys | Ala | Leu | Pro | Ala |
| | | | 195 | | | | | 200 | | | | | 205 | | |
| Pro | Ile | Glu | Lys | Thr | Ile | Ser | Lys | Ala | Lys | Gly | Gln | Pro | Arg | Glu | Pro |
| 210 | | | | | 215 | | | | | 220 | | | | | |
| Gln | Val | Tyr | Thr | Leu | Pro | Pro | Ser | Arg | Asp | Glu | Leu | Thr | Lys | Asn | Gln |
| 225 | | | | | 230 | | | | | 235 | | | | | 240 |
| Val | Ser | Leu | Thr | Cys | Leu | Val | Lys | Gly | Phe | Tyr | Pro | Ser | Asp | Ile | Ala |
| | | | | 245 | | | | | 250 | | | | | 255 | |
| Val | Glu | Trp | Glu | Ser | Asn | Gly | Gln | Pro | Glu | Asn | Asn | Tyr | Lys | Thr | Thr |
| | | | 260 | | | | | 265 | | | | | 270 | | |
| Pro | Pro | Val | Leu | Asp | Ser | Asp | Gly | Ser | Phe | Phe | Leu | Tyr | Ser | Lys | Leu |
| | | 275 | | | | | 280 | | | | | 285 | | | |
| Thr | Val | Asp | Lys | Ser | Arg | Trp | Gln | Gln | Gly | Asn | Val | Phe | Ser | Cys | Ser |
| | 290 | | | | 295 | | | | | 300 | | | | | |
| Val | Met | His | Glu | Ala | Leu | His | Asn | His | Tyr | Thr | Gln | Lys | Ser | Leu | Ser |
| 305 | | | | 310 | | | | | 315 | | | | | 320 | |
| Leu | Ser | Pro | | | | | | | | | | | | | |

```
<210> SEQ ID NO 39
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 39
```

-continued

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Cys Pro Pro Cys Pro Ala Pro Glu
            100                 105                 110

Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ala Pro Ile Glu Lys Thr Ile Ser Lys Ala Lys Gly Gln Pro Arg Glu
        210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro

<210> SEQ ID NO 40
<211> LENGTH: 323
<212> TYPE: PRT
<213> ORGANISM: Artificial
<220> FEATURE:
<223> OTHER INFORMATION: An artificially synthesized peptide sequence

<400> SEQUENCE: 40

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Cys Pro Pro Cys Pro Ala Pro Glu Leu
            100                 105                 110

Leu Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Lys Phe Asn Trp Tyr Val Asp Gly Val
145                 150                 155                 160

Glu Val His Asn Ala Lys Thr Lys Pro Arg Glu Glu Gln Tyr Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Ala Leu Pro Ala
        195                 200                 205

Pro Ile Glu Lys Thr Ile Ser Lys Ala Lys Gly Gln Pro Arg Glu Pro
    210                 215                 220

Gln Val Tyr Thr Leu Pro Pro Ser Arg Asp Glu Leu Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro

<210> SEQ ID NO 41
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 41

Gln Val Thr Leu Lys Glu Ser Gly Pro Thr Leu Val Lys Pro Thr Gln
  1               5                  10                  15

Thr Leu Thr Leu Thr Cys Ala Phe Ser Gly Phe Ser Leu Asn Thr Phe
             20                  25                  30

Asn Met Gly Ile Gly Trp Ile Arg Gln Pro Pro Gly Lys Ala Leu Glu
         35                  40                  45

Trp Leu Ala His Ile Trp Trp Asn Asp Asp Tyr Tyr Tyr His Pro Ser
     50                  55                  60

Leu Lys Ser Arg Leu Thr Ile Ser Lys Asp Ser Ser Lys Asn Gln Val
 65                  70                  75                  80
```

Asp Leu Thr Met Thr Asn Met Asp Pro Val Asp Thr Ala Thr Tyr Tyr
            85                  90                  95

Cys Ala Arg Ile Val Gly Glu Arg Ala Tyr Tyr Ser Asn Tyr Gly Phe
                100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Cys Cys Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 42
<211> LENGTH: 451
<212> TYPE: PRT
<213> ORGANISM: Artificial
<220> FEATURE:
<223> OTHER INFORMATION: An artificially synthesized peptide sequence

<400> SEQUENCE: 42

```
Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
    50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Thr Val Glu Arg Lys Cys Ser Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
```

```
                    405                 410                 415
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro
        450

<210> SEQ ID NO 43
<211> LENGTH: 452
<212> TYPE: PRT
<213> ORGANISM: Artificial
<220> FEATURE:
<223> OTHER INFORMATION: An artificially synthesized peptide sequence

<400> SEQUENCE: 43

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
            20                  25                  30

Asn Met Gly Ile Gly Trp Ile Arg Gln Pro Pro Gly Lys Ala Leu Glu
        35                  40                  45

Trp Leu Ala His Ile Trp Trp Asn Asp Asp Tyr Tyr His Pro Ser
 50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
            100                 105                 110

Ala Trp Phe Thr Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
```

```
                305                 310                 315                 320
Leu Asn Gly Lys Glu Tyr Lys Cys Lys Val Ser Asn Lys Ala Leu Pro
                    325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro
    450

<210> SEQ ID NO 44
<211> LENGTH: 451
<212> TYPE: PRT
<213> ORGANISM: Artificial
<220> FEATURE:
<223> OTHER INFORMATION: An artificially synthesized peptide sequence

<400> SEQUENCE: 44

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
                20                  25                  30

Asn Met Gly Ile Gly Trp Ile Arg Gln Pro Pro Gly Lys Ala Leu Glu
            35                  40                  45

Trp Leu Ala His Ile Trp Trp Asn Asp Asp Tyr Tyr Tyr His Pro Ser
        50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
                100                 105                 110

Ala Trp Phe Thr Tyr Trp Gly Gln Gly Thr Leu Val Thr Val Ser Ser
            115                 120                 125

Ala Ser Thr Lys Gly Pro Ser Val Phe Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
```

```
                210                 215                 220
Lys Val Glu Pro Lys Ser Cys Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
450

<210> SEQ ID NO 45
<211> LENGTH: 325
<212> TYPE: PRT
<213> ORGANISM: Artificial
<220> FEATURE:
<223> OTHER INFORMATION: An artificially synthesized peptide sequence

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Thr Val Glu Pro Lys Cys Ser Val Glu Cys Pro Pro Cys Pro Ala Pro
            100                 105                 110

Glu Leu Leu Gly Gly Pro Ser Val Phe Leu Phe Pro Pro Lys Pro Lys
```

```
            115                 120                 125
Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Ala Leu
                195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Lys Leu Thr Val Asp Lys Ser Arg Trp Gln Gln Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 46
<211> LENGTH: 453
<212> TYPE: PRT
<213> ORGANISM: Artificial
<220> FEATURE:
<223> OTHER INFORMATION: An artificially synthesized peptide sequence

<400> SEQUENCE: 46

Gln Val Thr Leu Lys Glu Ser Gly Pro Thr Leu Val Lys Pro Thr Gln
1               5                   10                  15

Thr Leu Thr Leu Thr Cys Ala Phe Ser Gly Phe Ser Leu Asn Thr Phe
                20                  25                  30

Asn Met Gly Ile Gly Trp Ile Arg Gln Pro Pro Gly Lys Ala Leu Glu
                35                  40                  45

Trp Leu Ala His Ile Trp Trp Asn Asp Asp Tyr Tyr Tyr His Pro Ser
                50                  55                  60

Leu Lys Ser Arg Leu Thr Ile Ser Lys Asp Ser Ser Lys Asn Gln Val
65                  70                  75                  80

Asp Leu Thr Met Thr Asn Met Asp Pro Val Asp Thr Ala Thr Tyr Tyr
                85                  90                  95

Cys Ala Arg Ile Val Gly Glu Arg Ala Tyr Tyr Ser Asn Tyr Gly Phe
                100                 105                 110

Ala Trp Phe Thr Tyr Trp Gly Gln Gly Thr Leu Val Thr Val Ser Ser
                115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
```

```
                145                 150                 155                 160
        Phe Pro Glu Pro Val Thr Val Ser Trp Asn Ser Gly Ala Leu Thr Ser
                        165                 170                 175
        Gly Val His Thr Phe Pro Ala Val Leu Gln Ser Ser Gly Leu Tyr Ser
                        180                 185                 190
        Leu Ser Ser Val Val Thr Val Pro Ser Ser Leu Gly Thr Gln Thr
                        195                 200                 205
        Tyr Ile Cys Asn Val Asn His Lys Pro Ser Asn Thr Lys Val Asp Lys
                        210                 215                 220
        Thr Val Glu Pro Lys Cys Ser Val Glu Cys Pro Pro Cys Pro Ala Pro
        225                 230                 235                 240
        Glu Leu Leu Gly Gly Pro Ser Val Phe Leu Phe Pro Pro Lys Pro Lys
                        245                 250                 255
        Asp Thr Leu Met Ile Ser Arg Thr Pro Glu Val Thr Cys Val Val Val
                        260                 265                 270
        Asp Val Ser His Glu Asp Pro Glu Val Lys Phe Asn Trp Tyr Val Asp
                        275                 280                 285
        Gly Val Glu Val His Asn Ala Lys Thr Lys Pro Arg Glu Glu Gln Tyr
                        290                 295                 300
        Asn Ser Thr Tyr Arg Val Val Ser Val Leu Thr Val Leu His Gln Asp
        305                 310                 315                 320
        Trp Leu Asn Gly Lys Glu Tyr Lys Cys Lys Val Ser Asn Lys Ala Leu
                        325                 330                 335
        Pro Ala Pro Ile Glu Lys Thr Ile Ser Lys Ala Lys Gly Gln Pro Arg
                        340                 345                 350
        Glu Pro Gln Val Tyr Thr Leu Pro Pro Ser Arg Asp Glu Leu Thr Lys
                        355                 360                 365
        Asn Gln Val Ser Leu Thr Cys Leu Val Lys Gly Phe Tyr Pro Ser Asp
                        370                 375                 380
        Ile Ala Val Glu Trp Glu Ser Asn Gly Gln Pro Glu Asn Asn Tyr Lys
        385                 390                 395                 400
        Thr Thr Pro Pro Val Leu Asp Ser Asp Gly Ser Phe Phe Leu Tyr Ser
                        405                 410                 415
        Lys Leu Thr Val Asp Lys Ser Arg Trp Gln Gln Gly Asn Val Phe Ser
                        420                 425                 430
        Cys Ser Val Met His Glu Ala Leu His Asn His Tyr Thr Gln Lys Ser
                        435                 440                 445
        Leu Ser Leu Ser Pro
            450

<210> SEQ ID NO 47
<211> LENGTH: 41
<212> TYPE: PRT
<213> ORGANISM: Homo sapiens

<400> SEQUENCE: 47

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Ser Cys Asp
                20                  25                  30

Lys Thr His Thr Cys Pro Pro Cys Pro
            35                  40

<210> SEQ ID NO 48
<211> LENGTH: 38
```

<212> TYPE: PRT
<213> ORGANISM: Artificial
<220> FEATURE:
<223> OTHER INFORMATION: An artificially synthesized peptide sequence

<400> SEQUENCE: 48

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Ser Cys Asp
            20                  25                  30

Lys Cys Pro Pro Cys Pro
        35

<210> SEQ ID NO 49
<211> LENGTH: 37
<212> TYPE: PRT
<213> ORGANISM: Artificial
<220> FEATURE:
<223> OTHER INFORMATION: An artificially synthesized peptide sequence

<400> SEQUENCE: 49

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Ser Cys Asp
            20                  25                  30

Cys Pro Pro Cys Pro
        35

<210> SEQ ID NO 50
<211> LENGTH: 36
<212> TYPE: PRT
<213> ORGANISM: Artificial
<220> FEATURE:
<223> OTHER INFORMATION: An artificially synthesized peptide sequence

<400> SEQUENCE: 50

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Ser Cys Cys
            20                  25                  30

Pro Pro Cys Pro
        35

<210> SEQ ID NO 51
<211> LENGTH: 34
<212> TYPE: PRT
<213> ORGANISM: Artificial
<220> FEATURE:
<223> OTHER INFORMATION: An artificially synthesized peptide sequence

<400> SEQUENCE: 51

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Cys Cys Pro Pro
            20                  25                  30

Cys Pro

<210> SEQ ID NO 52
<211> LENGTH: 38
<212> TYPE: PRT
<213> ORGANISM: Artificial
<220> FEATURE:
<223> OTHER INFORMATION: An artificially synthesized peptide sequence

```
<400> SEQUENCE: 52

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Cys Ser Asp
            20                  25                  30

Lys Cys Pro Pro Cys Pro
        35

<210> SEQ ID NO 53
<211> LENGTH: 38
<212> TYPE: PRT
<213> ORGANISM: Artificial
<220> FEATURE:
<223> OTHER INFORMATION: An artificially synthesized peptide sequence

<400> SEQUENCE: 53

Ser Ser Ser Leu Gly Thr Gln Thr Tyr Ile Cys Asn Val Asn His Lys
1               5                   10                  15

Pro Ser Asn Thr Lys Val Asp Lys Lys Val Glu Pro Lys Cys Ser Val
            20                  25                  30

Glu Cys Pro Pro Cys Pro
        35

<210> SEQ ID NO 54
<211> LENGTH: 38
<212> TYPE: PRT
<213> ORGANISM: Artificial
<220> FEATURE:
<223> OTHER INFORMATION: An artificially synthesized peptide sequence

<400> SEQUENCE: 54

Ser Ser Ser Leu Gly Thr Gln Thr Tyr Ile Cys Asn Val Asn His Lys
1               5                   10                  15

Pro Ser Asn Thr Lys Val Asp Lys Thr Val Glu Arg Lys Cys Ser Val
            20                  25                  30

Glu Cys Pro Pro Cys Pro
        35

<210> SEQ ID NO 55
<211> LENGTH: 38
<212> TYPE: PRT
<213> ORGANISM: Artificial
<220> FEATURE:
<223> OTHER INFORMATION: An artificially synthesized peptide sequence

<400> SEQUENCE: 55

Ser Ser Ser Leu Gly Thr Gln Thr Tyr Ile Cys Asn Val Asn His Lys
1               5                   10                  15

Pro Ser Asn Thr Lys Val Asp Lys Thr Val Glu Pro Lys Cys Ser Val
            20                  25                  30

Glu Cys Pro Pro Cys Pro
        35

<210> SEQ ID NO 56
<211> LENGTH: 38
<212> TYPE: PRT
<213> ORGANISM: Artificial
<220> FEATURE:
<223> OTHER INFORMATION: An artificially synthesized peptide sequence

<400> SEQUENCE: 56
```

```
Ser Ser Ser Leu Gly Thr Gln Thr Tyr Thr Cys Asn Val Asn His Lys
1               5                   10                  15

Pro Ser Asn Thr Lys Val Asp Lys Thr Val Glu Arg Lys Cys Ser Val
            20                  25                  30

Glu Cys Pro Pro Cys Pro
        35

<210> SEQ ID NO 57
<211> LENGTH: 38
<212> TYPE: PRT
<213> ORGANISM: Artificial
<220> FEATURE:
<223> OTHER INFORMATION: An artificially synthesized peptide sequence

<400> SEQUENCE: 57

Ser Ser Asn Phe Gly Thr Gln Thr Tyr Thr Cys Asn Val Asn His Lys
1               5                   10                  15

Pro Ser Asn Thr Lys Val Asp Lys Thr Val Glu Arg Lys Cys Ser Val
            20                  25                  30

Glu Cys Pro Pro Cys Pro
        35

<210> SEQ ID NO 58
<211> LENGTH: 36
<212> TYPE: PRT
<213> ORGANISM: Artificial
<220> FEATURE:
<223> OTHER INFORMATION: An artificially synthesized peptide sequence

<400> SEQUENCE: 58

Ser Ser Ser Leu Gly Thr Gln Thr Tyr Ile Cys Asn Val Asn His Lys
1               5                   10                  15

Pro Ser Asn Thr Lys Val Asp Lys Thr Val Glu Arg Lys Cys Ser Cys
            20                  25                  30

Pro Pro Cys Pro
        35
```